United States Patent [19]

Takemoto et al.

[11] 4,249,938
[45] Feb. 10, 1981

[54] N-PHENYL-N-METHYL-UREA DERIVATIVES, AND THEIR PRODUCTION AND USE

[75] Inventors: Ichiki Takemoto, Osaka; Seizo Sumida, Hyogo; Ryo Yoshida, Kawanishi; Katsuzo Kamoshita, Osaka, all of Japan

[73] Assignee: Sumitomo Chemical Company, Limited, Osaka, Japan

[21] Appl. No.: 919,683

[22] Filed: Jun. 27, 1978

[30] Foreign Application Priority Data

Jun. 28, 1977 [JP] Japan .................. 52-77400
Jul. 22, 1977 [JP] Japan .................. 52-88742
Feb. 28, 1978 [JP] Japan .................. 53-23026
Mar. 10, 1978 [JP] Japan .................. 53-27926

[51] Int. Cl.³ .................. A01N 47/30; A01N 31/08; C07C 119/20; C07C 127/19
[52] U.S. Cl. .................. 71/98; 71/91; 71/93; 71/111; 71/115; 71/116; 71/117; 71/120; 260/453 RW; 564/52
[58] Field of Search .......... 71/120, 98; 260/453 RW

[56] References Cited

U.S. PATENT DOCUMENTS

| | | | |
|---|---|---|---|
| 3,252,783 | 5/1966 | Newcomer et al. | 71/120 |
| 3,819,697 | 6/1974 | Cross | 71/120 |
| 4,123,256 | 10/1978 | Yoshida et al. | 260/453 RW |
| 4,129,436 | 12/1978 | Takemoto et al. | 260/453 RW |

FOREIGN PATENT DOCUMENTS 503459 4/1971 Switzerland .................. 71/120
532891 3/1973 Switzerland .................. 71/120

*Primary Examiner*—Glennon H. Hollrah
*Attorney, Agent, or Firm*—Birch, Stewart, Kolasch & Birch

[57] ABSTRACT

An N'-phenyl-N-methyl-urea derivative of the formula:

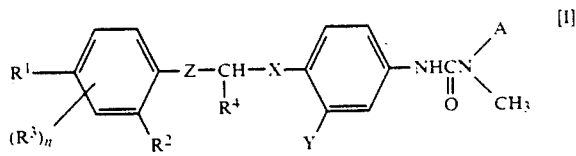

wherein $R^1$, $R^2$ and $R^3$ are each hydrogen, lower alkyl, lower alkoxy, lower alkylthio, halogen or trifluoromethyl, $R^4$ is hydrogen or lower alkyl, A is methyl or methoxy, X is oxygen or sulfur, Y is hydrogen or halogen, Z is a straight or branched alkylene chain having not more than 8 carbon atoms which may have no less than one atom of oxygen and/or sulfur inside and/or at the end of the alkylene chain and n is an integer of 1 to 3, which shows a pronounced herbicidal activity against a wide variety of weeds in the cultivation of crop plants without any material toxicity to mammals or fish or any chemical injury to said crop plants.

14 Claims, No Drawings

N-PHENYL-N-METHYL-UREA DERIVATIVES, AND THEIR PRODUCTION AND USE

The present invention relates to N'-phenyl-N-methyl-urea derivatives, and their production and use.

The N'-phenyl-N-methyl-urea derivatives of the present invention are representable by the formula:

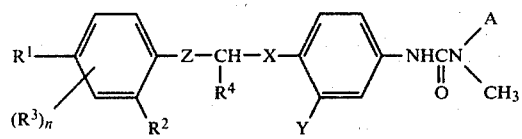

wherein $R^1$, $R^2$ and $R^3$ are each hydrogen, lower alkyl, lower alkoxy, lower alkylthio, halogen or trifluoromethyl, $R^4$ is hydrogen or lower alkyl, A is methyl or methoxy, X is oxygen or sulfur, Y is hydrogen or halogen, Z is a straight or branched alkylene chain having not more than 8 carbon atoms which may have no less than one atom of oxygen and/or sulfur inside and/or at the end of the alkylene chain and n is an integer of 1 to 3, with the following provisos:

(a) when $R^1$ is lower alkyl or lower alkoxy, $R^2$ is hydrogen or methyl, $R^4$ is hydrogen, A is methoxy, X is oxygen, Y is hydrogen and Z is methylene, $R^3$ is lower alkyl, lower alkoxy, halogen or trifluoromethyl;

(b) when $R^1$ is hydrogen, halogen or trifluoromethyl, $R^4$ is hydrogen, A is methoxy, X is oxygen, Y is hydrogen and Z is methylene, $R^2$ and $R^3$ are each hydrogen, lower alkyl, lower alkoxy, halogen or trifluoromethyl;

(c) when $R^4$ is hydrogen, A is methoxy, X is oxygen, Y is halogen and Z is methylene, $R^1$, $R^2$ and $R^3$ are each hydrogen, lower alkyl, lower alkoxy, halogen or trifluoromethyl;

(d) when $R^4$ is hydrogen, A is methyl, X is oxygen and Z is methylene, $R^1$, $R^2$ and $R^3$ are each hydrogen, lower alkyl, lower alkoxy, halogen or trifluoromethyl;

(e) when $R^4$ is hydrogen, X is sulfur and Z is methylene, $R^1$, $R^2$ and $R^3$ are each hydrogen, lower alkyl, lower alkoxy, halogen or trifluoromethyl;

(f) when $R^4$ is hydrogen, Z is a straight or branched alkylene chain having 2 to 8 carbon atoms or a straight or branched alkylene chain having 1 to 7 carbon atoms which may have no less than one atom of oxygen and/or sulfur inside and/or at the end of the alkylene chain; and (g) when $R^4$ is lower alkyl, Z is a straight or branched alkylene chain having 1 to 8 carbon atoms or a straight or branched chain having 1 to 7 carbon atoms which may have no less than one atom of oxygen and/or sulfur inside and/or at the end of the alkylene chain.

The term "lower" as hereinabove used in connection with alkyl, alkoxy or alkylthio is intended to mean a group having not more than 8 carbon atoms, particularly not more than 5 carbon atoms. Accordingly, the term "lower alkyl" includes methyl, ethyl, propyl, butyl, etc.; the term "lower alkoxy" covers methoxy, ethoxy, propoxy, butoxy, etc; and the term "lower alkylthio" may be, for instance, methylthio, ethylthio, propylthio or butylthio. The term "halogen" is intended to mean chlorine, bromine, fluorine, iodine, etc. Examples of the straight or branched alkylene chain which may have at least one of oxygen and sulfur in or at the end of the alkylene chain are as follows: ethylene, ethylidene, trimethylene, 2-methylethylene, 1-methylethylene, tetramethylene, 1-methyltrimethylene, 1,2-dimethylethylene, 2,2-dimethylethylene, pentamethylene, 2-methyltetramethylene, 3-methyltetramethylene, 2,3-dimethyltrimethylene, 2,2-dimethyltrimethylene, 3-ethyltrimethylene, hexamethylene, 5-methylpentamethylene, 2,4-dimethyltetramethylene, 3-ethyltetramethylene, 2,3,3-trimethyltrimethylene, 3-propyltrimethylene, heptamethylene, 2-methylhexamethylene, 4-methylhexamethylene, 5-methylhexamethylene, 2,5-dimethylpentamethylene, 3,5-dimethylpentamethylene, 5,5-dimethylpentamethylene, 4-ethylpentamethylene, 2,3,4-trimethyltetramethylene, 2,4,4-trimethyltetramethylene, 2-propyltetramethylene, octamethylene, 6-methylheptamethylene, 4,6-dimethylhexamethylene, 4-ethylhexamethylene, 2,4,5-trimethylpentamethylene, 2-methyl-5-ethylpentamethylene, methyleneoxy, methylenethio, 2-oxyethyl, 2-thioethyl, 1-oxyethyl, methyleneoxyethyl, methylenethiomethyl, 3-oxypropyl, 3-thiopropyl, 2-oxy-1-methylethyl, 2-(methyleneoxy)ethyl, (2-oxyethyl)oxymethyl, 4-oxybutyl, 3-oxy-1-methylpropyl, 2-oxy-1-ethylethyl, 3-methylenethiopropyl, (2-methyleneoxyethyl)oxymethyl, 5-oxypentyl, 5-thiopentyl, 3-oxy-1,3-dimethylpropyl, (3-oxypropyl)oxymethyl, (3-thiopropyl)oxymethyl, 3-(1-ethyleneoxy)propyl, 3-methoxypentamethylene, 2-(2-oxyethyloxy)ethyloxymethyl, 6-oxyhexyl, 3-(1-trimethyleneoxy)propyl, 7-oxyheptyl, 7-thioheptyl, etc. (the number indicating the position being the one calculated from the carbon atom on the phenylurea side as the starting point).

As is well known, soybeans, cotton, corn, wheat, rice, beets and the like are crops of world-wide importance. In cultivation of the said crop plants, chemical control of weeds is indispensable to prevent yield reduction. In recent years, the availability of selective herbicides which can exterminate weeds without any material chemical injury to desired crop plants is highly required.

Among substituted urea derivatives, as is well known, there are compounds having strong herbicidal activity such as N'-4-chlorophenyl-N,N-dimethylurea (monuron) and N'-3,4-dichlorophenyl-N,N-dimethylurea (diuron). It is also well known that the herbicidal activity of these urea derivatives is due to the inhibition of photosynthesis. Photosynthesis is a physiological function peculiar to higher plants and is not operative in mammals. Accordingly, it is highly possible that specific inhibitors of photosynthetic processes do no significant damage to mammals but can exterminate higher plants. In fact, herbicidal photosynthesis inhibitors such as monuron and diuron are all low in mammalian toxicity. However, they exert a herbicidal activity against all higher plants since photosynthesis is common to higher plants. As it is, most photosynthesis inhibitors are non-selective and do damage to crop plants. In order for a compound to be a selective herbicide, it has to have both strong herbicidal activity against weeds and a high level of selectivity to an intended crop. But, such a selective herbicide is very difficult to find and can not easily be thought out systematically by mere analogy and modification of known chemical structures. Therefore, a highly detailed study with trial and error is necessary to find such selective herbicides. For example, in the case of 2-chloro-4-ethylamino-6-isopropylamino-s-triazine (atrazine) having higher selectivity to corn, the chlorine atom at the 2-position is important to the selectivity. A compound having either a methoxy or methylthio group in place of the chlorine atom has very low selectivity to corn [H. Gysin: "The Chemical Structure and Biological Relationship of s-Triazines" in Pesticide Chemistry, Vol. 5, pages 1 to 27 (1972)]. N'-3,4-dichlorophenyl-N-methoxy-N-methylurea (linuron) has selectivity to some crops in the Umbelliferae family such as the carrot, but the compound having a methyl group in place of the methoxy group lacks the selectivity to the same plant [Herbicide Handbook of The Weed Science Society of America, 3rd Ed., pages 172 to 176 and 221 to 225 (1974)]. Selective herbicidal activity requires a very specific chemical structure, and only a slight difference in the chemical structure produces quite a large difference in degree and kind of selectivity.

The inventors chose to concentrate on phenylurea derivatives from the standpoint of low mammalian toxicity and strong herbicidal activity, and carried out an indepth investigation on how to impart selectivity to these derivatives. As the result, it has been found that the N'-phenyl-N-methyl-ureas [I] exhibit strongly herbicidal activity against many weeds by inhibition of photosynthesis and, besides, that they have high selectivity to rice plants and, depending on their kinds, to various other important crop plants.

While the N'-phenyl-N-methyl-ureas [I] are novel, there are known some compounds structurally similar thereto, of which examples are N'-(4-phenoxymethoxyphenyl)-N-methylurea [Swiss Pat. No. 532,891], N'-(4-benzyloxyphenyl)-N,N-dimethylurea [U.S. Pat. No. 3,819,697], N'-(4-benzylthiophenyl)-N,N-dimethylurea [U.S. Pat. No. 3,819,697], N'-(4-benzyloxyphenyl)-N-methoxy-N-methylurea [Japanese Patent Publication (unexamined) No. 52-111542], etc. Compared with these known N'-phenyl-N-methyl-urea derivatives, the N'-phenyl-N-methyl-ureas [I] are much more potent in herbicidal activity. Due to such high herbicidal potency, the N'-phenyl-N-methyl-ureas [I] can be used as herbicides not only in the cultivation field where a high selectivity is required but also in the non-cultivation field where a high selectivity is not necessarily required.

As stated above, the N'-phenyl-N-methyl-ureas [I] of the invention exhibit generally a strong herbicidal activity against a wide variety of weeds with a high selectivity to rice plants and show low mammalian and fish toxicity. Their selectivities to various crop plants other than rice plants vary more or less with their kinds, and some examples are as follows:

| N'-Phenyl-N-methyl-ureas [I] | Crop plants to which significant selectivity is shown |
|---|---|
| N'-4-[2-(2,5-Dimethylphenyl)ethoxy]phenyl-N-methoxy-N-methylurea | Soybean, wheat, cotton |
| N'-4-[2-(2-Methylphenyl)ethoxy]phenyl-N,N-dimethylurea | Soybean, wheat |
| N'-4-[2-(2-Fluorophenyl)ethoxy]phenyl-N-methoxy-N-methylurea | Corn, wheat |
| N'-4-[2-(3-Methoxyphenyl)ethoxy]phenyl-N-methoxy-N-methylurea | Soybean, cotton, corn |
| N'-4-[2-(4-Methylphenyl)ethoxy]phenyl-N,N-dimethylurea | Soybean, beet, wheat |
| N'-3-Chloro-4-[2-(4-methoxyphenyl)ethoxy]phenyl-N,N-dimethylurea | Soybean, beet |
| N'-4-[2-(3,4-Dimethylphenyl)ethoxy]phenyl-N,N-dimethylurea | Soybean, wheat |
| N'-4-[2-(4-Ethoxyphenyl)ethoxy]phenyl-N,N-dimethylurea | Soybean, cotton |
| N'-4-[2-(4-Isopropylphenyl)ethoxy]phenyl-N,N-dimethylurea | Soybean, beet, corn |
| N'-4-[2-(4-Methoxyphenyl)ethoxy]phenyl-N,N-dimethylurea | Soybean |
| N'-3-Chloro-4-[2-(4-ethoxyphenyl)ethoxy]phenyl-N,N-dimethylurea | Soybean |
| N'-4-[2-(4-Trifluoromethylphenyl)ethoxy]phenyl-N,N-dimethylurea | Cotton |
| N'-4-[2-(2,5-Dimethylphenyl)ethoxy]phenyl-N,N-dimethylurea | Wheat, barley |
| N'-4-[2-(3-Methylphenyl)ethoxy]phenyl-N,N-dimethylurea | Wheat |
| N'-4-[2-(4-tert-Butylphenyl)ethoxy]phenyl-N,N-dimethylurea | Corn |
| N'-3-Chloro-4-[2-(4-tert-butylphenyl)ethoxy]phenyl-N-methoxy-N-methylurea | Corn |
| N'-4-Phenethylthiophenyl-N,N-dimethylurea | Soybean, wheat |
| N'-4-[2-(2,4-Dimethylphenyl)ethylthio]phenyl-N,N-dimethylurea | Soybean, wheat, corn |
| N'-4-[2-(2-Methoxyphenyl)ethylthio]phenyl-N-methoxy-N-methylurea | wheat beet, corn |
| N'-4-(3-Phenylpropoxy)phenyl-N-methoxy-N-methylurea | Wheat |
| N'-4-[3-(2-Fluorophenyl)propoxy]phenyl-N,N-dimethylurea | Wheat |
| N'-4-[3-(4-Methylphenyl)propoxy]phenyl-N-methoxy-N-methylurea | Wheat |
| N'-3-Chloro-4-[3-(4-tert-butylphenyl)propoxy]phenyl-N-methoxy-N-methylurea | Cotton |
| N'-4-[2-Methyl-2-(4-methylphenyl)ethoxy]phenyl-N-methoxy-N-methylurea | Cotton, soybean |
| N'-4-(4-Phenylbutoxy)phenyl-N-methoxy-N-methylurea | Wheat |
| N'-3-Chloro-4-[4-(4-methoxyphenyl)butoxy]phenyl-N-methoxy-N-methylurea | Wheat |
| N'-4-(5-Phenylpentyloxy)phenyl-N-methoxy-N-methylurea | Wheat |
| N'-4-(7-Phenylheptyloxy)phenyl-N,N-dimethylurea | Wheat, beet |
| N'-4-(9-Phenylnonyloxy)phenyl-N,N-dimethylurea | Wheat, beet |
| N'-4-(Phenoxyethoxy)phenyl-N,N-dimethylurea | Soybean, wheat, cotton |
| N'-4-(3-Phenylpropoxy)phenyl-N,N-dimethylurea | Soybean, cotton, wheat |
| N'-3-Fluoro-4-[2-(4-methylphenyl)ethoxy]phenyl-N-methoxy-N-methylurea | Soybean, wheat |

Referring to the herbicidal activity of the N'-phenyl-N-methyl-ureas [I], they have a strong herbicidal activity on wide ranges of upland field weeds and paddy field weeds by both pre-emergence and post-emergence applications. For example, they exhibit strong herbicidal activity, at low concentrations, on various weeds such as broad-leaved weeds, e.g. redroot pigweed (*Amaranthus retroflexus*), common lambsquarter (*Chenopodium alubum*), cocklebur (*Xanthium pennsylvanicum*), annual morning glory (*Ipomoea purpurea*), chickweed (*Stellaria media*), radish (*Raphanus sativus*), pale smartweed (*Polygonum lapathiofolium*), toothcup (*Rotala indica*), pickerelweed (*Monochoria vaginalis*), false pimpernel (*Lindernia pyxidaria*), pitchfork (*Bidens frondosa*), black nightshade (*Solanum nigrum*), sunflower (*Helianthus annus*), jimson weed (*Datura stramonium*), velvetleaf (*Abutilon theophrasti*), etc., grassy weeds, e.g. goose grass (*Eleusine indica*), large crabgrass (*Digitaria sanguinalis*), barnyard grass (*Echinochloa crus-galli*), green foxtail (*Setaria viridis*), etc., and sedge weeds, e.g. nutsedge (*Cyperus difformis*), etc.

The N'-phenyl-N-methyl-ureas [I] can be manufactured by various procedures, among which those as shown in the following scheme are typical ones:

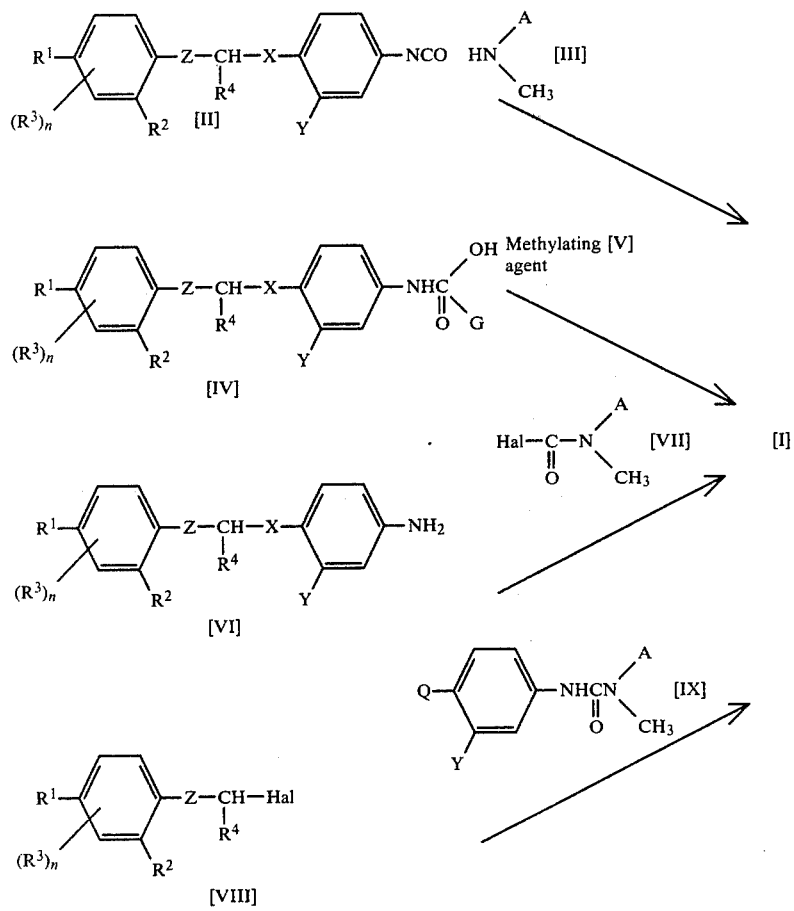

wherein G is hydrogen of methyl, Q is hydroxy or mercapto and Hal is hydrogen (e.g. chlorine, bromine), and $R^1$, $R^2$, $R^3$, $R^4$, A, X, Y, Z and n are each as defined above.

Namely, the N'-phenyl-N-methyl-urea [I] may be prepared by reacting the phenyl isocyanate [II] with the amine [III]. The reaction is usually carried out in the presence or absence of any solvent at a temperature within a wide range, e.g. under cooling, at room temperature or while heating (usually up to 100° C.). The reaction time depends on the reaction temperature, the reagent, etc. and is varied in a range of from about 1 to 10 hours. As the solvent, there may be employed water or an organic solvent (e.g. benzene, toluene, xylene, diethyl ether, tetrahydrofuran, dioxane, chloroform, carbon tetrachloride, ethyl acetate, pyridine, dimethylformamide), or their mixtures. When water is employed as the solvent, the amine [III] may be used in the form of an aqueous solution so that the objective compound is obtainable in a good yield.

In an alternative way, the N'-phenyl-N-methyl-urea [I] may be prepared by reacting the N-hydroxyurea [IV] with a methylating agent [V]. Examples of the methylating agent are methyl iodide, dimethyl sulfate, diazomethane, etc. The reaction may be carried out in an inert solvent at a temperature within a wide range, e.g. under cooling, at room temperature or while heating (usually up to 100° C.). In case of the methylating agent being dimethyl sulfate, the inert solvent may be water or an organic solvent (e.g. benzene, toluene, xylene, methanol, ethanol, isopropanol, diethyl ether, tetrahydrofuran, dioxane), or their mixtures. The existence of an alkali such as sodium hydroxide or potassium hydroxide is advantageous in effecting the reaction smoothly. The existence of a phase transfer catalyst such as benzyltriethylammonium chloride or tetra-n-butylammonium bromide is also advantageous in the reaction. The reaction time depends on the reaction temperature, the methylating agent, etc. and is usually from about 0.5 to 10 hours.

In another alternative way, the N'-phenyl-N-methyl-urea [I] may be prepared by reacting the phenylamine [VI] with the carbamyl halide [VII]. The reaction may be carried out in the presence or absence of an inert solvent, preferably in the coexistence of an acid eliminating agent, at a temperature within a wide range, e.g. under cooling, at room temperature or while heating (usually up to 150° C.). As the inert solvent, there may be used water or an organic solvent (e.g. benzene, toluene, xylene, diethyl ether, tetrahydrofuran, dioxane, chloroform, carbon tetrachloride, methylene chloride, ethyl acetate, methanol, ethanol, isopropanol, dimethylformamide), or their mixtures. Examples of the acid eliminating agent are organic bases (e.g. pyridine, triethylamine), inorganic bases (e.g. sodium hydroxide, potassium hydroxide, sodium carbonate), etc. The reaction time depends on the reaction temperature and is usually from about 0.5 to 10 hours.

In a further alternative way, the N'-phenyl-N-methylurea [I] may be prepared by reacting the alkyl halide [VIII] with the phenylurea [IX]. The reaction may be carried out usually in an inert solvent in the presence of an acid eliminating agent at a temperature within a wide range, e.g. under cooling, at room temperature or while heating (usually up to 150° C.). Examples of the inert solvent are an organic solvent (e.g. benzene, toluene, xylene, diethyl ether, tetrahydrofuran, dioxane, chloroform, carbon tetrachloride, methylene chloride, ethyl acetate, methanol, ethanol, isopropanol, dimethylformamide) or water, or their mixtures. As the acid eliminating agent, there may be exemplified pyridine, triethylamine, sodium hydroxide, potassium hydroxide, sodium carbonate, etc. The reaction time depends on the reaction temperature and is usually from about 0.5 to 10 hours.

In the above procedures, the phenyl isocyanate [II] is obtainable by reacting the phenylamine [VI] with phosgene. The N-hydroxyurea [IV] is obtainable by reacting the phenyl isocyanate [II] with hydroxylamine or N-methylhydroxylamine.

Some embodiments of the procedures for preparation of the N'-phenyl-N-methyl-ureas [I] are illustratively shown in the following Examples.

EXAMPLE 1

To a solution of 4-[2-(4-chlorophenyl)ethoxy]phenyl isocyanate (3.5 g) in benzene (100 ml), a solution of N,O-dimethylhydroxylamine (1.5 g) in benzene (50 ml) was added dropwise at a temperature of 20° to 30° C. After the dropwise addition was completed, the resultant mixture was stirred at the same temperature for an additional 30 minutes. The reaction mixture was concentrated under reduced pressure, and the residue was crystallized from ethanol to give N'-4-[2-(4-chlorophenyl)ethoxy]phenyl-N-methoxy-N-methylurea (Compound No. 9) as white needles (2.9 g) melting at 77° to 78° C.

EXAMPLE 2

To a solution of 3-chloro-4-[2-(4-chlorophenyl)ethoxy]phenyl isocyanate (4 g) in benzene (100 ml), a solution of N,O-dimethylhydroxylamine (2 g) in benzene (50 ml) was added dropwise at a temperature below 30° C. The resulting mixture was allowed to stand at room temperature for 30 minutes and then concentrated under reduced pressure. The residue was crystallized from ethanol to give N'-3-chloro-4-[2-(4-chlorophenyl)ethoxy]-phenyl-N-methoxy-N-methylurea (Compound No. 28) as white needles (2.7 g) melting at 99° to 100° C.

EXAMPLE 3

To a solution of 4-[2-(4-methylphenyl)ethoxy]phenyl isocyanate (30 g) in benzene (300 ml), a solution of dimethylamine (11 g) in benzene (100 ml) was added dropwise at a temperature below 30° C. The resultant mixture was allowed to stand at room temperature for 1 hour and then concentrated under reduced pressure. The residue was crystallized from ethanol to give N'-4-[2-(4-methylphenyl)ethoxy]phenyl-N,N-dimethylurea (Compound No. 30) as white needles (20 g) melting at 152° to 153° C.

EXAMPLE 4

To a solution of 4-phenethylthiophenyl isocyanate (25.5 g) in benzene (100 ml), a solution of N,O-dimethylhydroxylamine (9 g) in benzene (50 ml) was added dropwise at a temperature below 30° C. The resultant mixture was allowed to stand at room temperature for 30 minutes, and then concentrated under reduced pressure. The residue was crystallized from ethanol to give N'-4-phenethylthiophenyl-N-methoxy-N-methylurea (Compound No. 56) as white needles (28.4 g) melting at 85° to 85.5° C.

EXAMPLE 5

To a solution of 4-(5-phenylpentoxy)phenyl isocyanate (28.1 g) in benzene (100 ml), a solution of N,O-dimethylhydroxylamine (9.1 g) in benzene (50 ml) was added dropwise at a temperature of 20° to 30° C. The resultant mixture was stirred at the same temperature for 30 minutes and then concentrated under reduced pressure. The residue was crystallized from ethanol to give N'-4-(5-phenylpentoxy)phenyl-N-methoxy-N-methylurea (Compound No. 95) as white needles (30.3 g) melting at 82.5° to 83° C.

EXAMPLE 6

To a solution of 4-[2-(2-methoxyphenyl)ethoxy]phenyl isocyanate (4.7 g) in methylene chloride (50 ml), a solution of hydroxylamine hydrochloride (7 g) and sodium hydroxide (4 g) in water (15 ml) was added dropwise at a temperature below 20° C. The precipitated crystals were collected by filtration and dried to give N'-4-[2-(2-methoxyphenyl)ethoxy]phenyl-N-hydroxyurea (4.5 g). To a solution of the hydroxyurea derivative (4.5 g), dimethyl sulfate (4.2 g) and tetra-n-butylammonium bromide (0.05 g) in toluene (60 ml) was added dropwise an aqueous solution of sodium hydroxide (10 N, 5.4 ml) at a temperature below 22° C. The resultant mixture was stirred at room temperature, diluted with water and extracted with benzene. After removal of the solvent under reduced pressure, the residue was crystallized from ethanol to give N'-4-[2-(2-methoxyphenyl)ethoxy]phenyl-N-methoxy-N-methylurea (Compound No. 4) as white needles (4.4 g) melting at 63° to 64° C.

EXAMPLE 7

To a solution of 3-chloro-4-[2-(4-methoxyphenyl)ethoxy]phenyl isocyanate (6 g) in methylene chloride (80 ml), a solution of hydroxylamine hydrochloride (7 g) and sodium hydroxide (4 g) in water (15 ml) was added dropwise at a temperature below 20° C. The precipitated crystals were collected by filtration and dried to give N'-3-chloro-4-[2-(4-methoxyphenyl)ethoxy]phenyl-N-hydroxyurea (5.6 g). This hydroxyurea derivative (5.6 g) was dissolved in a mixture of benzene and methanol (1:1 by volume) (250 ml), and 10 N sodium hydroxide solution (4 ml) and dimethyl sulfate (3.2 ml) were added dropwise thereto at a temperature below 30° C. The resultant mixture was stirred at room temperature, diluted with water and extracted with benzene. After removal of the solvent under reduced pressure, the residue was crystallized from ethanol to give N'-3-chloro-4-[2-(4-methoxyphenyl)ethoxy]phenyl-N-methoxy-N-methylurea (Compound No. 43) as white needles (3.2 g) melting at 51° to 52° C.

EXAMPLE 8

To a solution of 4-[2-(4-methylphenyl)ethylthio]phenyl isocyanate (13.5 g) in methylene chloride (50 ml), a solution of hydroxylamine hydrochloride (7 g) and sodium hydroxide (4 g) in water (15 ml) was added dropwise at a temperature below 20° C. The resultant mixture was diluted with water. The precipitated crystals were collected by filtration and dried to give N'-4-[2-(4-methylphenyl)ethylthio]phenyl-N-hydroxyurea (14.5 g). This hydroxyurea derivative (14.5 g) was dissolved in a mixture of benzene and methanol (1:1 by volume) (200 ml), and 10 N sodium hydroxide solution (10 ml) and dimethyl sulfate (12 g) were added dropwise thereto at a temperature below 30° C. The resultant mixture was stirred at room temperature, diluted with water and extracted with benzene. After removal of the solvent under reduced pressure, the residue was crystallized from ethanol to give N'-4-[2-(4-methylphenyl)ethylthio]phenyl-N-methoxy-N-methylurea (Compound No. 58) as white needles (11.9 g) melting at 74.5° to 75° C.

EXAMPLE 9

A solution of 4-[3-(3,4-dichlorophenyl)propoxy]phenyl isocyanate (32.2 g) in methylene chloride (50 ml) was added dropwise to a solution of hydroxylamine hydrochloride (8.9 g) and sodium hydroxide (5.2 g) in water (20 ml) at a temperature below 20° C. The reaction mixture was diluted with water, and the precipitated crystals were collected by filtration and dried to give N'-4-[3-(3,4-dichlorophenyl)propoxy]phenyl-N-hydroxyurea (34.3 g). The hydroxyurea derivative was dissolved in a mixture of benzene and methanol (1:1 by volume) (200 ml), 10 N sodium hydroxide solution (19 ml) and dimethyl sulfate (25.2 g) were alternatively added dropwise thereto at a temperature below 30° C., and stirring was continued at room temperature. The reaction mixture was diluted with water and extracted with benzene. The benzene extract was washed with water, concentrated under reduced pressure and crystallized from ethanol to give N'-4-[3-(3,4-dichlorophenyl)propoxy]phenyl-N-methoxy-N-methylurea (Compound No. 75) as white crystals (35.3 g) melting at 95° to 96° C.

EXAMPLE 10

To a solution of sodium ethoxide (5.2 g) in N,N-dimethylformamide (100 ml), N'-4-hydroxyphenyl-N-methoxy-N-methylurea (15 g) was added, and a solution of 2-(2,5-dimethylphenyl)ethyl bromide (16.3 g) in N,N-dimethylformamide (50 ml) was added dropwise thereto. The resulting mixture was gradually heated up to 90° C. and maintained at this temperature for 3 hours. The reaction mixture was poured into ice-water and extracted with benzene. The benzene extract was concentrated under reduced pressure, and the residue was crystallized from ethanol to give N'-4-[2-(2,5-dimethylphenyl)ethoxy]phenyl-N-methoxy-N-methylurea (Compound No. 10) as white needles (8.8 g) melting at 115° to 115.5° C.

EXAMPLE 11

To a solution of sodium ethoxide (2.7 g) in N,N-dimethylformamide (100 ml), N'-(3-chloro-4-hydroxy)phenyl-N,N-dimethylurea (8.6 g) was added, and a solution of 2-(3-methyl-4-methoxyphenyl)ethyl bromide (9.2 g) in N,N-dimethylformamide (50 ml) was added dropwise thereto. The resulting mixture was gradually heated up to 90°-100° C., and kept at this temperature for 3.5 hours. The reaction mixture was poured into ice-water and extracted with benzene. The benzene extract was concentrated under reduced pressure, and the residue was crystallized from ethanol to give N'-3-chloro-4-[2-(3-methyl-4-methoxyphenyl)ethoxy]phenyl-N,N-dimethylurea (Compound No. 53) as white needles (5.2 g) melting at 114° to 116° C.

EXAMPLE 12

A solution of 4-[2-(3-chlorophenyl)ethylthio]aniline (26.4 g), N,N-dimethylcarbamyl chloride (11.3 g) and pyridine (50 ml) in toluene (300 ml) was heated under reflux for 7 hours. The reaction mixture was diluted with water, and the toluene layer was separated, washed with dilute hydrochloric acid and water, dried over anhydrous sodium sulfate and concentrated under reduced pressure. The residue was crystallized from ethanol to give N'-4-[2-(3-chlorophenyl)ethylthio]phenyl-N,N-dimethylurea (Compound No. 65) as white needles (25 g) melting at 107° to 108° C.

EXAMPLE 13

To a solution of 4-(9-phenyl-n-nonyloxy)aniline (14.8 g) in toluene (300 ml), 40% sodium hydroxide solution (55 ml) and N,N-dimethylcarbamyl chloride (8 g) were added, and the resulting mixture was refluxed for 10 hours. After cooling to room temperature, the toluene layer was separated and washed with water, followed by concentration under reduced pressure. The residue was crystallized from ethanol to give N'-4-(9-phenyl-n-nonyloxy)phenyl-N,N-dimethylurea (Compound No. 106) as white crystals (13.7 g) melting at 79° to 81° C.

EXAMPLE 14

To a solution of sodium ethoxide (6.8 g) in N,N-dimethylformamide (200 ml), N'-4-mercaptophenyl-N,N-dimethylurea (20 g) was added, and a solution of 2-(2,4-dimethylphenyl)ethyl bromide (22 g) in N,N-dimethylformamide (100 ml) was added dropwise thereto. The resultant mixture was gradually heated up to 100° C. and kept at this temperature for 5 hours. The reaction mixture was poured into ice-water and extracted with benzene. The benzene extract was concentrated under reduced pressure, and the residue was crystallized with ethanol to give N'-4-[2-(2,4-dimethylphenyl)ethylthio]phenyl-N,N-dimethylurea (Compound No. 61) as white needles (25.8 g) melting at 95° to 96° C.

EXAMPLE 15

To a solution of sodium ethoxide (6.8 g) in N,N-dimethylformamide (200 ml), N'-(4-hydroxyphenyl)-N,N-dimethylurea (18 g) was added, and a solution of 2-(3-trifluoromethylphenoxy)ethyl bromide (29.5 g) in N,N-dimethylformamide (100 ml) was added dropwise thereto. The temperature was gradually elevated up to 100° C., and the reaction mixture was maintained at this temperature for 5 hours and then poured into ice water. The precipitated crystals were collected by filtration, washed with water, ethanol and ether, dried and recrystallized from ethanol to give N'-4-[2-(3-trifluoromethylphenoxy)ethoxy]phenyl-N,N-dimethylurea (Compound No. 113) as white crystals (33.3 g) melting at 127° to 128° C.

Specific examples of the N'-phenyl-N-methyl-ureas [I], which can be prepared in the same manner as above, are as follows:

| No. | Structure | Melting point (°C.) or $n_D$ |
|---|---|---|
| 1 | C6H5—CH2CH2O—C6H4—NHC(O)N(OCH3)(CH3) | 79–80 |
| 2 | 2-F-C6H4—CH2CH2O—C6H4—NHC(O)N(OCH3)(CH3) | 64–65 |
| 3 | 2-CH3-C6H4—CH2CH2O—C6H4—NHC(O)N(OCH3)(CH3) | 69–70 |
| 4 | 2-OCH3-C6H4—CH2CH2O—C6H4—NHC(O)N(OCH3)(CH3) | 63–64 |
| 5 | 3-Cl-C6H4—CH2CH2O—C6H4—NHC(O)N(OCH3)(CH3) | 88–89 |
| 6 | 3-CH3-C6H4—CH2CH2O—C6H4—NHC(O)N(OCH3)(CH3) | 96.0–96.5 |
| 7 | 3-CH3O-C6H4—CH2CH2O—C6H4—NHC(O)N(OCH3)(CH3) | 96–97 |
| 8 | 4-F-C6H4—CH2CH2O—C6H4—NHC(O)N(OCH3)(CH3) | 87–88 |
| 9 | 4-Cl-C6H4—CH2CH2O—C6H4—NHC(O)N(OCH3)(CH3) | 77–78 |
| 10 | 2,5-(CH3)2-C6H3—CH2CH2O—C6H4—NHC(O)N(OCH3)(CH3) | 115.0–115.5 |
| 11 | 4-CF3-C6H4—CH2CH2O—C6H4—NHC(O)N(OCH3)(CH3) | 93.0–93.5 |
| 12 | 3-CH3-4-CH3O-C6H3—CH2CH2O—C6H4—NHC(O)N(OCH3)(CH3) | 94–95 |
| 13 | 3,4-(CH3)2-C6H3—CH2CH2O—C6H4—NHC(O)N(OCH3)(CH3) | 112.5–113.0 |
| 14 | 4-Br-C6H4—CH2CH2O—C6H4—NHC(O)N(OCH3)(CH3) | 78.0–78.5 |
| 15 | C6H5—CH2CH2O—C6H4—NHC(O)N(CH3)(CH3) | 143–144 |

-continued

| No. | Structure | Melting point (°C.) or $n_D$ |
|---|---|---|
| 16 | ⌬—CH₂CH₂O—⌬(Cl)—NHCN(OCH₃)(CH₃), C=O | 59–60 |
| 17 | ⌬—CH₂CH₂O—⌬(Cl)—NHCN(CH₃)(CH₃), C=O | 108–109 |
| 18 | ⌬(F)—CH₂CH₂O—⌬—NHCN(CH₃)(CH₃), C=O | 119–120 |
| 19 | ⌬(CH₃)—CH₂CH₂O—⌬—NHCN(CH₃)(CH₃), C=O | 127.5–128.0 |
| 20 | ⌬(Cl)—CH₂CH₂O—⌬—NHCN(CH₃)(CH₃), C=O | 117–119 |
| 21 | ⌬(Cl)—CH₂CH₂O—⌬(Cl)—NHCN(OCH₃)(CH₃), C=O | 57–58 |
| 22 | ⌬(Cl)—CH₂CH₂O—⌬(Cl)—NHCN(CH₃)(CH₃), C=O | 100.0–100.5 |
| 23 | ⌬(CH₃)—CH₂CH₂O—⌬—NHCN(CH₃)(CH₃), C=O | 106–107 |
| 24 | ⌬(CH₃)—CH₂CH₂O—⌬(Cl)—NHCN(OCH₃)(CH₃), C=O | 16–19 |
| 25 | ⌬(CH₃)—CH₂CH₂O—⌬(Cl)—NHCN(CH₃)(CH₃), C=O | 96.0–98.5 |
| 26 | F—⌬—CH₂CH₂O—⌬—NHCN(CH₃)(CH₃), C=O | 127.0–127.5 |
| 27 | Cl—⌬—CH₂CH₂O—⌬—NHCN(CH₃)(CH₃), C=O | 129.0–130.5 |
| 28 | Cl—⌬—CH₂CH₂O—⌬(Cl)—NHCN(OCH₃)(CH₃), C=O | 99–100 |
| 29 | Cl—⌬—CH₂CH₂O—⌬(Cl)—NHCN(CH₃)(CH₃), C=O | 129–130 |

-continued

| No. | Structure | Melting point (°C.) or $n_D$ |
|---|---|---|
| 30 | CH₃—⟨phenyl⟩—CH₂CH₂O—⟨phenyl⟩—NHC(=O)N(CH₃)(CH₃) | 152–153 |
| 31 | CH₃—⟨phenyl⟩—CH₂CH₂O—⟨phenyl, Cl⟩—NHC(=O)N(OCH₃)(CH₃) | 76–77 |
| 32 | CH₃—⟨phenyl⟩—CH₂CH₂O—⟨phenyl, Cl⟩—NHC(=O)N(CH₃)(CH₃) | 112.0–112.5 |
| 33 | C₂H₅—⟨phenyl⟩—CH₂CH₂O—⟨phenyl⟩—NHC(=O)N(CH₃)(CH₃) | 148–149 |
| 34 | C₂H₅—⟨phenyl⟩—CH₂CH₂O—⟨phenyl, Cl⟩—NHC(=O)N(OCH₃)(CH₃) | 22–23 |
| 35 | C₂H₅—⟨phenyl⟩—CH₂CH₂O—⟨phenyl, Cl⟩—NHC(=O)N(CH₃)(CH₃) | 110–111 |
| 36 | i-C₃H₇—⟨phenyl⟩—CH₂CH₂O—⟨phenyl⟩—NHC(=O)N(CH₃)(CH₃) | 126–127 |
| 37 | i-C₃H₇—⟨phenyl⟩—CH₂CH₂O—⟨phenyl, Cl⟩—NHC(=O)N(OCH₃)(CH₃) | 5–6 |
| 38 | i-C₃H₇—⟨phenyl⟩—CH₂CH₂O—⟨phenyl, Cl⟩—NHC(=O)N(CH₃)(CH₃) | 118–121 |
| 39 | t-C₄H₉—⟨phenyl⟩—CH₂CH₂O—⟨phenyl⟩—NHC(=O)N(CH₃)(CH₃) | 86–87 |
| 40 | t-C₄H₉—⟨phenyl⟩—CH₂CH₂O—⟨phenyl, Cl⟩—NHC(=O)N(OCH₃)(CH₃) | 70–72 |
| 41 | t-C₄H₉—⟨phenyl⟩—CH₂CH₂O—⟨phenyl, Cl⟩—NHC(=O)N(CH₃)(CH₃) | 146–148 |
| 42 | CH₃O—⟨phenyl⟩—CH₂CH₂O—⟨phenyl⟩—NHC(=O)N(CH₃)(CH₃) | 128–129 |
| 43 | CH₃O—⟨phenyl⟩—CH₂CH₂O—⟨phenyl, Cl⟩—NHC(=O)N(OCH₃)(CH₃) | 51–52 |
| 44 | CH₃O—⟨phenyl⟩—CH₂CH₂O—⟨phenyl, Cl⟩—NHC(=O)N(CH₃)(CH₃) | 131–132 |

-continued

| No. | Structure | Melting point (°C.) or n_D |
|---|---|---|
| 45 | $C_2H_5O$—〇—$CH_2CH_2O$—〇—NHC(=O)N(CH_3)(CH_3) | 149–150 |
| 46 | $C_2H_5O$—〇—$CH_2CH_2O$—〇(Cl)—NHC(=O)N(OCH_3)(CH_3) | 62–63 |
| 47 | $C_2H_5O$—〇—$CH_2CH_2O$—〇(Cl)—NHC(=O)N(CH_3)(CH_3) | 107–109 |
| 48 | $CF_3$—〇—$CH_2CH_2O$—〇—NHC(=O)N(CH_3)(CH_3) | 125–126 |
| 49 | 2,5-(CH_3)_2-C_6H_3—$CH_2CH_2O$—〇—NHC(=O)N(CH_3)(CH_3) | 146–147 |
| 50 | 3,4-(CH_3)_2-C_6H_3—$CH_2CH_2O$—〇—NHC(=O)N(CH_3)(CH_3) | 135–136 |
| 51 | 3-CH_3-4-CH_3O-C_6H_3—$CH_2CH_2O$—〇—NHC(=O)N(CH_3)(CH_3) | 150–151 |
| 52 | 3-CH_3-4-CH_3O-C_6H_3—$CH_2CH_2O$—〇(Cl)—NHC(=O)N(OCH_3)(CH_3) | 61–62 |
| 53 | 3-CH_3-4-CH_3O-C_6H_3—$CH_2CH_2O$—〇(Cl)—NHC(=O)N(CH_3)(CH_3) | 114–116 |
| 54 | 2-Cl-C_6H_4—$CH_2CH_2O$—〇(Cl)—NHC(=O)N(CH_3)(CH_3) | 124–125 |
| 55 | 3,4-Cl_2-C_6H_3—$CH_2CH_2O$—〇(Cl)—NHC(=O)N(OCH_3)(CH_3) | 104–105 |
| 56 | C_6H_5—$CH_2CH_2S$—〇—NHC(=O)N(OCH_3)(CH_3) | 85–85.5 |
| 57 | C_6H_5—$CH_2CH_2S$—〇—NHC(=O)N(CH_3)(CH_3) | 136–137 |
| 58 | $CH_3$—〇—$CH_2CH_2S$—〇—NHC(=O)N(OCH_3)(CH_3) | 74.5–75 |
| 59 | $CH_3$—〇—$CH_2CH_2S$—〇—NHC(=O)N(CH_3)(CH_3) | 145–146 |

-continued

| No. | Structure | Melting point (°C.) or $n_D$ |
|---|---|---|
| 60 | CH₃-(2,4-diMe-C₆H₃)-CH₂CH₂S-C₆H₄-NHC(=O)N(OCH₃)(CH₃) | 78–79 |
| 61 | CH₃-(2,4-diMe-C₆H₃)-CH₂CH₂S-C₆H₄-NHC(=O)N(CH₃)(CH₃) | 95–96 |
| 62 | (2-OCH₃-C₆H₄)-CH₂CH₂S-C₆H₄-NHC(=O)N(OCH₃)(CH₃) | 67–68.5 |
| 63 | (2-OCH₃-C₆H₄)-CH₂CH₂S-C₆H₄-NHC(=O)N(CH₃)(CH₃) | 120–121 |
| 64 | (3-Cl-C₆H₄)-CH₂CH₂S-C₆H₄-NHC(=O)N(OCH₃)(CH₃) | 56–57 |
| 65 | (3-Cl-C₆H₄)-CH₂CH₂S-C₆H₄-NHC(=O)N(CH₃)(CH₃) | 107–108 |
| 66 | (4-CH₃-C₆H₄)-CH₂CH₂S-(3-Cl-C₆H₃)-NHC(=O)N(OCH₃)(CH₃) | 105–106 |
| 67 | (4-CH₃-C₆H₄)-CH₂CH₂S-(3-Cl-C₆H₃)-NHC(=O)N(CH₃)(CH₃) | 141–142 |
| 68 | C₆H₅-(CH₂)₃-O-C₆H₄-NHC(=O)N(OCH₃)(CH₃) | 79–80 |
| 69 | (2-F-C₆H₄)-(CH₂)₃-O-C₆H₄-NHC(=O)N(OCH₃)(CH₃) | 69–70 |
| 70 | (2-F-C₆H₄)-(CH₂)₃-O-C₆H₄-NHC(=O)N(CH₃)(CH₃) | 132–133 |
| 71 | (2-F-C₆H₄)-(CH₂)₃-O-(3-Cl-C₆H₃)-NHC(=O)N(OCH₃)(CH₃) | 50–51 |
| 72 | (2-F-C₆H₄)-(CH₂)₃-O-(3-Cl-C₆H₃)-NHC(=O)N(CH₃)(CH₃) | 112–115 |
| 73 | (4-Cl-C₆H₄)-(CH₂)₃-O-C₆H₄-NHC(=O)N(OCH₃)(CH₃) | 118–119 |
| 74 | (4-Cl-C₆H₄)-(CH₂)₃-O-C₆H₄-NHC(=O)N(CH₃)(CH₃) | 142–143 |

| No. | Structure | Melting point (°C.) or $n_D$ |
|---|---|---|
| 75 | Cl-C₆H₃(Cl)-(CH₂)₃-O-C₆H₄-NHC(O)N(OCH₃)(CH₃) | 95–96 |
| 76 | Cl-C₆H₃(Cl)-(CH₂)₃-O-C₆H₄-NHC(O)N(CH₃)(CH₃) | 115–116 |
| 77 | H₃C-C₆H₄-(CH₂)₃-O-C₆H₄-NHC(O)N(OCH₃)(CH₃) | 93–94.5 |
| 78 | H₃C-C₆H₄-(CH₂)₃-O-C₆H₄-NHC(O)N(CH₃)(CH₃) | 137–138 |
| 79 | t-C₄H₉-C₆H₄-(CH₂)₃-O-C₆H₄-NHC(O)N(CH₃)(CH₃) | 138–139 |
| 80 | t-C₄H₉-C₆H₄-(CH₂)₃-O-C₆H₃(Cl)-NHC(O)N(OCH₃)(CH₃) | $n_D^{24}$ 1.5442 |
| 81 | t-C₄H₉-C₆H₄-(CH₂)₃-O-C₆H₃(Cl)-NHC(O)N(CH₃)(CH₃) | $n_D^{24.5}$ 1.5558 |
| 82 | H₃C-C₆H₄-CH(CH₃)CH₂O-C₆H₄-NHC(O)N(OCH₃)(CH₃) | 83–84 |
| 83 | H₃C-C₆H₄-CH(CH₃)CH₂O-C₆H₄-NHC(O)N(CH₃)(CH₃) | 102–103 |
| 84 | C₆H₅-CH₂-CH(CH₃)-O-C₆H₄-NHC(O)N(OCH₃)(CH₃) | $n_D^{27}$ 1.5651 |
| 85 | Cl-C₆H₄-(CH₂)₃-S-C₆H₄-NHC(O)N(OCH₃)(CH₃) | 127–128 |
| 86 | Cl-C₆H₄-(CH₂)₃-S-C₆H₄-NHC(O)N(CH₃)(CH₃) | 104–105 |
| 87 | C₆H₅-(CH₂)₄-O-C₆H₄-NHC(O)N(OCH₃)(CH₃) | 79–80 |
| 88 | H₃CO-C₆H₄-(CH₂)₄-O-C₆H₃(Cl)-NHC(O)N(OCH₃)(CH₃) | 76.5–78 |
| 89 | H₃C-C₆H₄-C(CH₃)₂-CH₂-O-C₆H₄-NHC(O)N(OCH₃)(CH₃) | $n_D^{25}$ 1.5541 |
| 90 | H₃C-C₆H₄-C(CH₃)₂-CH₂-O-C₆H₄-NHC(O)N(CH₃)(CH₃) | $n_D^{25}$ 1.5653 |

-continued

| No. | Structure | Melting point (°C.) or $n_D$ |
|---|---|---|
| 91 | 4-Cl-C$_6$H$_4$-CH(CH$_3$)-CH$_2$CH$_2$S-C$_6$H$_4$-NHC(O)N(OCH$_3$)(CH$_3$) | $n_D^{24}$ 1.5831 |
| 92 | 4-Cl-C$_6$H$_4$-CH(CH$_3$)-CH$_2$CH$_2$S-C$_6$H$_4$-NHC(O)N(CH$_3$)$_2$ | 85–86 |
| 93 | 4-CH$_3$-C$_6$H$_4$-(CH$_2$)$_4$-O-C$_6$H$_4$-NHC(O)N(OCH$_3$)(CH$_3$) | 27–28 |
| 94 | 4-H$_3$C-C$_6$H$_4$-(CH$_2$)$_4$-O-C$_6$H$_4$-NHC(O)N(CH$_3$)$_2$ | 131–132 |
| 95 | C$_6$H$_5$-(CH$_2$)$_5$-O-C$_6$H$_4$-NHC(O)N(OCH$_3$)(CH$_3$) | 82.5–83 |
| 96 | C$_6$H$_5$-(CH$_2$)$_5$-O-C$_6$H$_4$-NHC(O)N(CH$_3$)$_2$ | 110–111 |
| 97 | C$_6$H$_5$-CH(C$_2$H$_5$)-CH$_2$O-(3-F-C$_6$H$_3$)-NHC(O)N(OCH$_3$)(CH$_3$) | $n_D^{25}$ 1.5298 |
| 98 | C$_6$H$_5$-CH(C$_2$H$_5$)-CH$_2$O-(3-F-C$_6$H$_3$)-NHC(O)N(CH$_3$)$_2$ | $n_D^{25}$ 1.5495 |
| 99 | C$_6$H$_5$-CH$_2$-CH(CH$_3$)-(CH$_2$)$_2$-O-(3-Cl-C$_6$H$_3$)-NHC(O)N(OCH$_3$)(CH$_3$) | $n_D^{24}$ 1.5620 |
| 100 | C$_6$H$_5$-(CH$_2$)$_5$-S-C$_6$H$_4$-NHC(O)N(OCH$_3$)(CH$_3$) | 51–52.5 |
| 101 | C$_6$H$_5$-(CH$_2$)$_5$-S-C$_6$H$_4$-NHC(O)N(CH$_3$)$_2$ | 65–66.5 |
| 102 | 4-H$_3$C-C$_6$H$_4$-CH(CH$_3$)-CH(CH$_3$)-CH$_2$O-C$_6$H$_4$-NHC(O)N(OCH$_3$)(CH$_3$) | 90–92 |
| 103 | C$_6$H$_5$-(CH$_2$)$_7$-O-C$_6$H$_4$-NHC(O)N(OCH$_3$)(CH$_3$) | 72–73 |
| 104 | C$_6$H$_5$-(CH$_2$)$_7$-O-C$_6$H$_4$-NHC(O)N(CH$_3$)$_2$ | 96–97 |
| 105 | C$_6$H$_5$-(CH$_2$)$_9$-O-C$_6$H$_4$-NHC(O)N(OCH$_3$)(CH$_3$) | 65–67 |
| 106 | C$_6$H$_5$-(CH$_2$)$_9$-O-C$_6$H$_4$-NHC(O)N(CH$_3$)$_2$ | 79–81 |

| No. | Structure | Melting point (°C.) or $n_D$ |
|---|---|---|
| 107 | 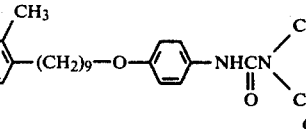 | 36–38 |
| 108 | 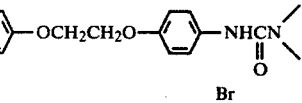 | 66–69 |
| 109 | 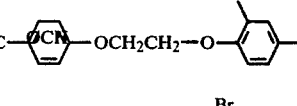 | 162–163 |
| 110 | 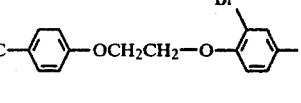 | 152–153 |
| 111 | 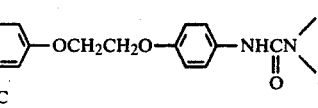 | 128–129 |
| 112 | 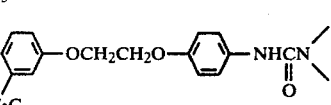 | 115–116 |
| 113 | 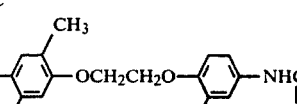 | 127–128 |
| 114 | 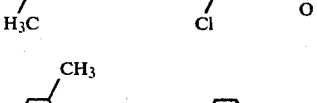 | 138–139 |
| 115 | 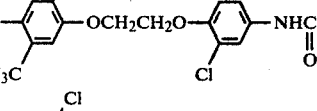 | 135–136 |
| 116 | 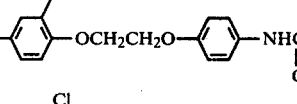 | 135–137 |
| 117 | 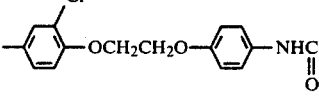 | 155–156 |
| 118 | 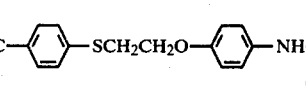 | 93–94 |
| 119 | 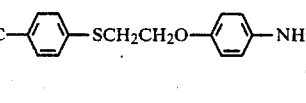 | 113–114.5 |
| 120 | 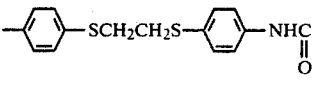 | 96–98 |
| 121 | 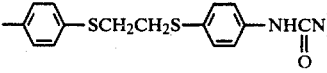 | 135–137 |

-continued

| No. | Structure | Melting point (°C.) or $n_D$ |
|---|---|---|
| 122 | F,F,F,F,F-C6-OCH2CH2O-C6H4-NHC(O)N(OCH3)(CH3) | 81–82 |
| 123 | F,F,F,F,F-C6-OCH2CH2O-C6H4-NHC(O)N(CH3)(CH3) | 59–60 |
| 124 | H3C-C6H4-OCH2CH2CH2O-C6H4-NHC(O)N(OCH3)(CH3) | 112–113 |
| 125 | H3C-C6H4-OCH2CH2CH2O-C6H4-NHC(O)N(CH3)(CH3) | 169–170 |
| 126 | 3,5-Cl2-C6H3-OCH2CH2OCH2CH2O-C6H4-NHC(O)N(OCH3)(CH3) | 80–81 |
| 127 | 3,5-Cl2-C6H3-OCH2CH2OCH2CH2O-C6H4-NHC(O)N(CH3)(CH3) | 109–110 |
| 128 | H3CS-C6H4-OCH2CH2OCH2CH2S-C6H4-NHC(O)N(OCH3)(CH3) | 41–42 |
| 129 | H3C-C6H4-OCH2CH2SCH2CH2O-C6H4-NHC(O)N(OCH3)(CH3) | $n_D^{23}$ 1.5705 |
| 130 | H3C-C6H4-OCH2CH2SCH2CH2O-C6H4-NHC(O)N(CH3)(CH3) | $n_D^{25}$ 1.5865 |
| 131 | C6H5-CH2OCH2-C(CH3)2-CH2S-C6H4-NHC(O)N(OCH3)(CH3) | $n_D^{24}$ 1.5519 |
| 132 | C6H5-CH2OCH2-C(CH3)2-CH2S-C6H4-NHC(O)N(CH3)(CH3) | 61–62 |
| 133 | CH3S-C6H4-OCH2CH2OCH2CH2S-C6H4-NHC(O)N(CH3)(CH3) | 80–81 |
| 134 | C6H5-O(CH2)8-O-C6H4-NHC(O)N(OCH3)(CH3) | 65–66 |
| 135 | C6H5-O(CH2)8-O-C6H4-NHC(O)N(CH3)(CH3) | 73–74 |
| 136 | C6H5-(CH2)3-O-C6H3(Cl)-NHC(O)N(OCH3)(CH3) | 29–30 |

-continued

| No. | Structure | Melting point (°C.) or $n_D$ |
|---|---|---|
| 137 | Ph—(CH$_2$)$_3$—O—C$_6$H$_3$(Cl)—NHC(=O)N(CH$_3$)$_2$ | 99–100 |
| 138 | (2-Cl-C$_6$H$_4$)—CH$_2$CH$_2$O—C$_6$H$_4$—NHC(=O)N(OCH$_3$)(CH$_3$) | 51–52 |
| 139 | (2-Cl-C$_6$H$_4$)—CH$_2$CH$_2$O—C$_6$H$_4$—NHC(=O)N(CH$_3$)$_2$ | 115–116 |
| 140 | Ph—(CH$_2$)$_4$—O—C$_6$H$_4$—NHC(=O)N(CH$_3$)$_2$ | 102–103 |
| 141 | Ph—(CH$_2$)$_3$—O—C$_6$H$_4$—NHC(=O)N(CH$_3$)$_2$ | 127–128 |
| 142 | CH$_3$—C$_6$H$_4$—CH$_2$CH$_2$O—C$_6$H$_3$(F)—NHC(=O)N(OCH$_3$)(CH$_3$) | 71–72 |
| 143 | CH$_3$—C$_6$H$_4$—CH$_2$CH$_2$O—C$_6$H$_3$(F)—NHC(=O)N(CH$_3$)$_2$ | 139–140 |

In the practical usage of the N'-phenyl-N-methyl-ureas [I], they may be applied as they are or may be applied in any of the formulation forms such as wettable powders, emulsifiable concentrates, granules, dusts and the like.

In preparing such formulation forms, a solid or liquid carrier may be used. As for the solid carrier, there may be mentioned mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like.

As for the liquid carrier, there may be mentioned alcohols (e.g. methyl alcohol, ethyl alcohol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methyl ethyl ketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water, etc.

A surface active agent to be used for emulsification, dispersion and spreading may be any of the nonionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene polymers, oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts, oxyalkylamines and the like. But the surface active agent is not of course limited to these compounds. And, if necessary, gelatin, casein, sodium alginate, starch, agar, polyvinyl alcohol or the like may be used as an auxiliary agent.

Practical embodiments of the herbicidal composition according to the present invention are illustratively shown in the following examples, wherein parts and % are by weight. The Compound Numbers correspond to those as shown above.

EXAMPLE A

Twenty five parts of Compound No. 1 or 56, 2.5 parts of a dodecylbenzenesulfonate, 2.5 parts of a lignin sulfonate and 70 parts of diatomaceous earth are well mixed while being powdered to obtain a wettable powder formulation.

EXAMPLE B

Eighty parts of Compound No. 28, 5 parts of a surface active agent (polyoxyethylene alkylaryl ether type) and 15 parts of talc are well mixed while being powdered to obtain a wettable powder formulation.

EXAMPLE C

Eighty parts of Compound No. 85, 5 parts of a surface active agent (polyoxyethylene alkylaryl ether type) and 15 parts of synthetic silicic acid are well mixed while being powdered to obtain a wettable powder formulation.

EXAMPLE D

Thirty parts of Compound No. 4, 10 parts of an emulsifier "Sorpol SM" (trade name, manufactured by Toho Chemical Co., Ltd.) and 60 parts of xylene are well mixed to obtain an emulsifiable concentrate formulation.

EXAMPLE E

Five parts of Compound No. 30, 20 parts of a surface active agent (polyethylene glycol ether type) and 75 parts of benzene are well mixed to obtain an emulsifiable concentrate formulation.

EXAMPLE F

Thirty parts of Compound No. 57 or 87, 7 parts of a polyoxyethylene alkylaryl ether, 3 parts of an alkylaryl sulfonate and 60 parts of xylene are well mixed to obtain an emulsifiable concentrate formulation.

EXAMPLE G

Five parts of Compound No. 9 or 59, 1 part of white carbon, 5 parts of a lignin sulfonate and 89 parts of clay are well mixed while being powdered. The mixture is then well kneaded with the addition of water, granulated and dried to obtain a granular formulation.

EXAMPLE H

Five parts of Compound No. 43, 40 parts of bentonite, 50 parts of clay and 5 parts of sodium lignin sulfonate are well mixed while being powdered. The mixture is then well kneaded with the addition of water, granulated and dried to obtain a granular formulation.

EXAMPLE J

One part of Compound No. 89, 1 part of white carbon, 5 parts of a lignin sulfonate and 93 parts of clay are well mixed while being powdered. The mixture is then well kneaded with the addition of water, granulated and dried to obtain a granular formulation.

EXAMPLE K

Forty parts of bentonite, 5 parts of a lignin sulfonate and 55 parts of clay are well mixed while being powdered. The mixture is then well kneaded with the addition of water, granulated and dried to obtain granules. The granules (95 parts) are impregnated with 5 parts of Compound No. 63 or 69 to obtain a granular formulation.

EXAMPLE L

Three parts of Compound No. 12, 65 or 77, 1 part of isopropyl phosphate, 66 parts of clay and 30 parts of talc are well mixed while being powdered to obtain a dust formulation.

EXAMPLE M

Three parts of Compound No. 53 and 97 parts of clay are well mixed while being powdered to obtain a dust formulation.

The N'-phenyl-N-methyl-ureas [I] may be used in admixture with other herbicides to improve their activity as herbicides, and in some cases, a synergistic effect can be obtained. As the other herbicides, there may be mentioned phenoxy herbicides such as 2,4-dichlorophenoxyacetic acid, 2-methyl-4-chlorophenoxyacetic acid and 2,4-dichlorophenoxybutyric acid (including esters and salts thereof); diphenyl ether herbicides such as 2,4-dichlorophenyl-4'-nitrophenyl ether, 2,4,6-trichlorophenyl-4'-nitrophenyl ether, 2,4-dichlorophenyl-4'-nitro-3'-methoxyphenyl ether and 2,4-dichlorophenyl-3'-methoxycarbonyl-4'-nitrophenyl ether; triazine herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine and 2-methylthio-4,6-bisisopropylamino-1,3,5-triazine; triazinone herbicides such as 4-amino-6-tert-butyl-3-methylthio-1,2,4-triazin-5(4H)-one; substituted urea herbicides such as N'-(3,4-dichlorophenyl)-N,N-dimethylurea, N'-(3,4-dichlorophenyl)-N-methoxy-N-methylurea, N'-(3-chloro-4-difluorochloromethylthiophenyl)-N,N-dimethylurea, N'-[4-(4-chlorophenoxy)-phenyl]-N,N-dimethylurea and N'-($\alpha,\alpha,\alpha$-trifluoro-m-tolyl)-N,N-dimethylurea; carbamate herbicides such as isopropyl-N-(3-chlorophenyl)carbamate, methyl-N-(3,4-dichlorophenyl)carbamate and 4-chloro-2-butynyl-N-(3-chlorophenyl)carbamate; thiolcarbamate herbicides such as S-(4-chlorobenzyl)-N,N-diethylthiolcarbamate, S-ethyl-N,N-hexamethylenethiolcarbamate and S-ethyl dipropylthiolcarbamate; acid anilide herbicides such as 3,4-dichloropropionanilide, N-methoxymethyl-2,6-diethyl-2-chloroacetanilide and 2-chloro-2',6'-diethyl-N-(butoxymethyl)acetanilide; uracil herbicides such as 5-bromo-3-sec-butyl-6-methyluracil and 3-cyclohexyl-5,6-trimethyleneuracil; pyridinium salt herbicides such as 1,1'-dimethyl-4,4'-bispyridinium dichloride; organo-phosphorus herbicides such as N-(phosphonomethyl)glycine, O-ethyl-O-(2-nitro-5-methylphenyl)-N-sec-butylphosphoroamidothioate and O-methyl-O-(2-nitro-4-methylphenyl)-N-isopropylphosphoroamidothioate; toluidine herbicides such as $\alpha,\alpha,\alpha$-trifluoro-2,6-dinitro-N,N-dipropyl-p-toluidine and N-(cyclopropylmethyl)-$\alpha,\alpha,\alpha$-trifluoro-2,6-dinitro-N-propyl-p-toluidine; N-sec-butyl-4-tert-butyl-2,6-dinitroaniline; 3,5-dinitro-N,N-dipropylsulfanylamide; 5-tert-butyl-3-(2,4-dichloro-5-isopropoxyphenyl)-1,3,4-oxadiazolin-2-one; 3-isopropyl-1H-2,1,3-benzothiadiazin-(4)-3H-one-2,2-dioxide (including salts thereof); $\alpha$-($\beta$-naphthoxy)propionanilide; 2-($\alpha$-naphthoxy)-N,N-diethylpropionamide; 3-amino-2,5-dichlorobenzoic acid, 2-sec-butyl-4,6-dinitrophenol; N-1-naphthylphthalamic acid; 2-(1-allyloxyamino)butylidene-5,5-dimethyl-4-methoxycarbonylcyclohexane-1,3-dione (including salts thereof) and the like. But, the herbicides are not of course limited to these examples.

The herbicides of the present invention may be applied together with fungicides, microbial insecticides, pyrethroid series insecticides, other synthetic insecticides, plant growth regulators or fertilizers.

The concentration of the N'-phenyl-N-methyl-ureas [I] as the active ingredient in the herbicidal composition is usually from about 1 to 80% by weight, although higher or lower concentrations may be employed.

When the N'-phenyl-N-methyl-ureas [I] are applied as a herbicide, the application method and the dosage rate depend upon the type of formulation of the active ingredient, the kinds of crop plants being cultivated, the kinds of weeds to be killed, the weather conditions, etc. It is preferably applied to both weeds and crop plants over the top in the post-emergence treatment, but it may be applied at any time ranging from the stage immediately after sowing. The dosage rate is generally about 2 to 80 grams, preferably 5 to 40 grams, of the active ingredient per are. For instance, the application to a cultivated land may be carried out with weeds of about 1 to 15 cm in height at a dose of about 2 to 80 grams per are by over-the-top foliar treatment. Further, for instance, the application to a paddy field may be carried out within 4 weeks after the transplantation of the seedlings of rice plants with a dose of the active ingredient in an amount of about 2 to 80 grams per are by water treatment.

The following examples show some typical test data indicating the excellent herbicidal activity of the N'-phenyl-N-methyl-ureas [I]. The compound Numbers correspond to those as shown above. The compounds for comparison are as follows:

evaluation of herbicidal activity and crop damage was made on the rice plants and the barnyard grass cultivated as well as nutsedge and broad-leaved weeds (e.g. pickerelweed, false pimpernel, toothcup) which emerged spontaneously. The results are shown in Table 1. Herbicidal activity and crop damage were evaluated as follows: the aereal parts of the test plants were cut off and weighed (fresh weight); the percentage of the fresh weight of the treated plant to that of the untreated plant was calculated with the latter fresh weight taken as 100; and the crop damage and herbicidal activity were eval-

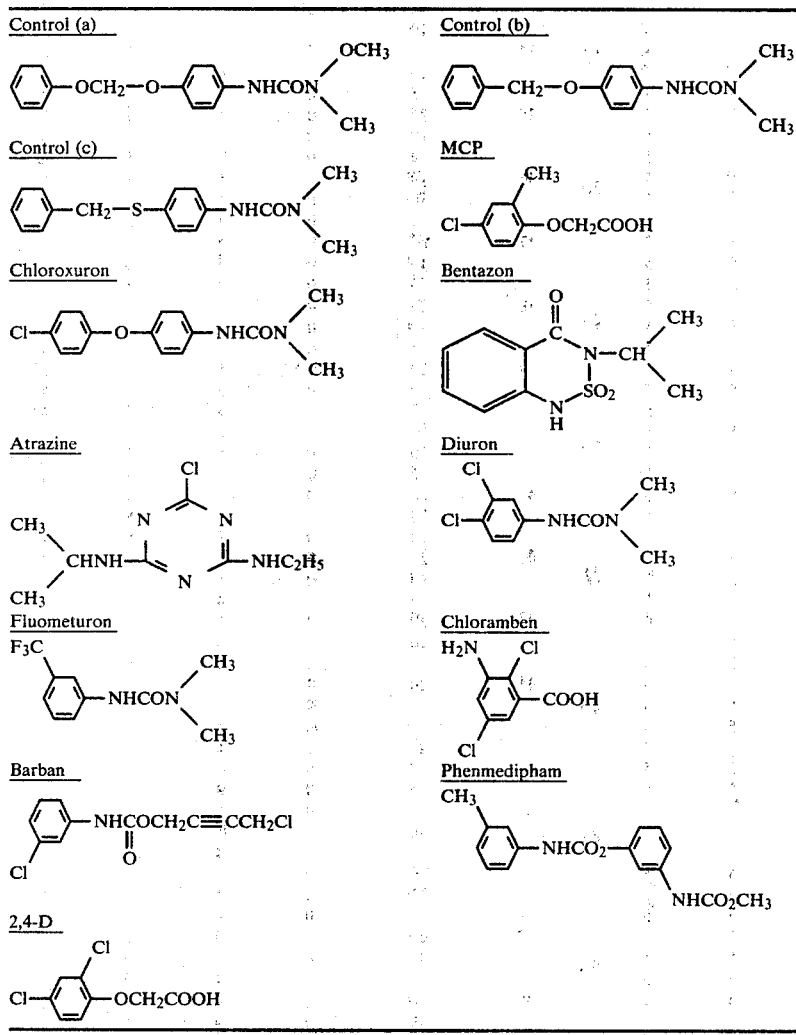

EXAMPLE I

Herbicidal activity and selectivity to rice plant under paddy conditions:

Wagner's pots (1/5000 are) were filled with paddy field soil (1.5 kg/pot) and kept under flooded conditions. Seedlings of rice plants at a three-leaf stage were transplanted thereto, and the seeds of barnyard grass were sowed therein and grown up for 5 days. Thereafter, the designed amount of the test compound was applied to the water layer. In applying the test compound, its designed amount was formulated into a wettable powder, diluted with water and applied to the water layer at a rate of 15 ml per pot by means of a pipette. Twenty five days after the application, the uated by the standard given in the table below:

| Rating value | 0 | 1 | 2 | 3 | 4 | 5 |
|---|---|---|---|---|---|---|
| Degree of herbicidal activity | None | Slight (plants recovered from damage) | Low | Moderate | High | Complete death |
| Fresh weight (% of the untreated) | 100 | 99-81 | 80-51 | 50-21 | 20-1 | 0 |

TABLE 1

| Compound No. | Dosage (weight of active ingredient, g/are) | Phytotoxicity Rice plant | Herbicidal activity Barnyard grass | Herbicidal activity Broad-leaved weeds | Herbicidal activity Nut-sedge |
|---|---|---|---|---|---|
| 1 | 20 | 0 | 4 | 5 | 5 |
|   | 10 | 0 | 3 | 4 | 5 |
| 2 | 20 | 1 | 5 | 5 | 5 |
|   | 10 | 0 | 5 | 5 | 5 |
| 3 | 20 | 0 | 5 | 5 | 5 |
|   | 10 | 0 | 4 | 5 | 5 |
| 4 | 20 | 0 | 5 | 5 | 5 |
|   | 10 | 0 | 4 | 5 | 5 |
| 5 | 20 | 0 | 5 | 5 | 5 |
|   | 10 | 0 | 4 | 5 | 5 |
| 6 | 20 | 0 | 5 | 5 | 5 |
|   | 10 | 0 | 5 | 5 | 5 |
| 7 | 20 | 0 | 4 | 5 | 5 |
|   | 10 | 0 | 4 | 5 | 5 |
| 8 | 20 | 0 | 5 | 5 | 5 |
|   | 10 | 0 | 4 | 5 | 5 |
| 9 | 20 | 0 | 5 | 5 | 5 |
|   | 10 | 0 | 5 | 5 | 5 |
| 10 | 20 | 0 | 4 | 5 | 5 |
|   | 10 | 0 | 4 | 5 | 5 |
| 11 | 20 | 0 | 5 | 5 | 5 |
|   | 10 | 0 | 5 | 5 | 5 |
| 12 | 20 | 0 | 5 | 5 | 5 |
|   | 10 | 0 | 4 | 5 | 5 |
| 13 | 20 | 0 | 5 | 5 | 5 |
|   | 10 | 0 | 5 | 5 | 5 |
| 14 | 20 | 0 | 5 | 5 | 5 |
|   | 10 | 0 | 5 | 5 | 5 |
| 15 | 20 | 0 | 5 | 5 | 5 |
|   | 10 | 0 | 5 | 5 | 5 |
|   | 5 | 0 | 5 | 5 | 5 |
| 16 | 20 | 0 | 5 | 5 | 5 |
|   | 10 | 0 | 5 | 5 | 5 |
|   | 5 | 0 | 4 | 5 | 5 |
| 17 | 20 | 0 | 5 | 5 | 5 |
|   | 10 | 0 | 5 | 5 | 5 |
|   | 5 | 0 | 4 | 5 | 4 |
| 18 | 10 | 1 | 5 | 5 | 5 |
|   | 5 | 0 | 5 | 5 | 5 |
|   | 2.5 | 0 | 5 | 5 | 5 |
| 19 | 20 | 0 | 5 | 5 | 5 |
|   | 10 | 0 | 5 | 5 | 5 |
|   | 5 | 0 | 4 | 5 | 5 |
| 20 | 10 | 0 | 5 | 5 | 5 |
|   | 5 | 0 | 5 | 5 | 5 |
|   | 2.5 | 0 | 5 | 5 | 5 |
| 21 | 20 | 0 | 5 | 5 | 5 |
|   | 10 | 0 | 5 | 5 | 5 |
|   | 5 | 0 | 5 | 5 | 5 |
| 22 | 20 | 0 | 5 | 5 | 5 |
|   | 10 | 0 | 5 | 5 | 5 |
|   | 5 | 0 | 5 | 5 | 5 |
| 23 | 20 | 1 | 5 | 5 | 5 |
|   | 10 | 0 | 5 | 5 | 5 |
|   | 5 | 0 | 5 | 5 | 5 |
| 24 | 20 | 0 | 5 | 5 | 5 |
|   | 10 | 0 | 5 | 5 | 5 |
|   | 5 | 0 | 4 | 5 | 5 |
| 25 | 20 | 0 | 5 | 5 | 5 |
|   | 10 | 0 | 4 | 5 | 5 |
|   | 5 | 0 | 4 | 5 | 4 |
| 26 | 10 | 0 | 5 | 5 | 5 |
|   | 5 | 0 | 5 | 5 | 5 |
|   | 2.5 | 0 | 5 | 5 | 5 |
| 27 | 10 | 0 | 5 | 5 | 5 |
|   | 5 | 0 | 5 | 5 | 5 |
|   | 2.5 | 0 | 5 | 5 | 5 |
| 28 | 20 | 0 | 5 | 5 | 5 |
|   | 10 | 0 | 5 | 5 | 5 |
|   | 5 | 0 | 5 | 5 | 5 |
| 29 | 20 | 0 | 5 | 5 | 5 |
|   | 10 | 0 | 5 | 5 | 5 |
|   | 5 | 0 | 4 | 5 | 5 |
| 30 | 20 | 0 | 5 | 5 | 5 |
|   | 10 | 0 | 5 | 5 | 4 |
|   | 5 | 0 | 3 | 5 | 4 |
| 31 | 20 | 0 | 5 | 5 | 5 |
|   | 10 | 0 | 5 | 5 | 5 |
|   | 5 | 0 | 4 | 5 | 5 |
| 32 | 20 | 0 | 5 | 5 | 5 |
|   | 10 | 0 | 4 | 5 | 5 |
|   | 5 | 0 | 4 | 5 | 5 |
| 33 | 40 | 0 | 5 | 5 | 5 |
|   | 20 | 0 | 5 | 5 | 4 |
|   | 10 | 0 | 4 | 5 | 4 |
| 34 | 20 | 0 | 5 | 5 | 5 |
|   | 10 | 0 | 4 | 5 | 4 |
|   | 5 | 0 | 4 | 5 | 4 |
| 35 | 20 | 0 | 5 | 5 | 5 |
|   | 10 | 0 | 5 | 5 | 5 |
|   | 5 | 0 | 3 | 5 | 4 |
| 36 | 20 | 0 | 5 | 5 | 5 |
|   | 10 | 0 | 5 | 5 | 4 |
|   | 5 | 0 | 4 | 5 | 4 |
| 37 | 20 | 0 | 5 | 5 | 5 |
|   | 10 | 0 | 5 | 5 | 5 |
|   | 5 | 0 | 3 | 5 | 5 |
| 38 | 20 | 0 | 5 | 5 | 5 |
|   | 10 | 0 | 4 | 5 | 5 |
|   | 5 | 0 | 3 | 5 | 4 |
| 39 | 20 | 0 | 5 | 5 | 5 |
|   | 10 | 0 | 5 | 5 | 5 |
|   | 5 | 0 | 3 | 5 | 4 |
| 40 | 20 | 0 | 5 | 5 | 5 |
|   | 10 | 0 | 5 | 5 | 5 |
|   | 5 | 0 | 4 | 5 | 4 |
| 41 | 40 | 0 | 5 | 5 | 5 |
|   | 20 | 0 | 5 | 5 | 5 |
|   | 10 | 0 | 3 | 5 | 4 |
| 42 | 20 | 1 | 5 | 5 | 5 |
|   | 10 | 0 | 5 | 5 | 5 |
|   | 5 | 0 | 4 | 5 | 5 |
| 43 | 20 | 1 | 5 | 5 | 5 |
|   | 10 | 0 | 5 | 5 | 5 |
|   | 5 | 0 | 4 | 5 | 3 |
| 44 | 20 | 0 | 5 | 5 | 5 |
|   | 10 | 0 | 5 | 5 | 5 |
|   | 5 | 0 | 5 | 5 | 3 |
| 45 | 20 | 0 | 5 | 5 | 5 |
|   | 10 | 0 | 5 | 5 | 5 |
|   | 5 | 0 | 4 | 5 | 4 |
| 46 | 20 | 0 | 5 | 5 | 5 |
|   | 10 | 0 | 5 | 5 | 5 |
|   | 5 | 0 | 4 | 5 | 5 |
| 47 | 20 | 0 | 5 | 5 | 5 |
|   | 10 | 0 | 4 | 5 | 5 |
|   | 5 | 0 | 4 | 5 | 5 |
| 48 | 20 | 0 | 5 | 5 | 5 |
|   | 10 | 0 | 5 | 5 | 5 |
|   | 5 | 0 | 4 | 5 | 5 |
| 49 | 20 | 0 | 4 | 5 | 5 |
|   | 10 | 0 | 4 | 5 | 5 |
|   | 5 | 0 | 4 | 5 | 3 |
| 50 | 20 | 0 | 5 | 5 | 5 |
|   | 10 | 0 | 5 | 5 | 5 |
|   | 5 | 0 | 4 | 5 | 4 |
| 51 | 40 | 0 | 5 | 5 | 5 |
|   | 20 | 0 | 4 | 5 | 5 |
|   | 10 | 0 | 4 | 5 | 4 |
| 52 | 20 | 1 | 5 | 5 | 5 |
|   | 10 | 0 | 5 | 5 | 5 |
|   | 5 | 0 | 5 | 5 | 5 |
| 53 | 10 | 0 | 5 | 5 | 5 |
|   | 5 | 0 | 5 | 5 | 5 |
|   | 2.5 | 0 | 5 | 5 | 5 |
| 54 | 20 | 0 | 5 | 5 | 5 |
|   | 10 | 0 | 5 | 5 | 5 |
|   | 5 | 0 | 3 | 5 | 4 |
| 55 | 20 | 0 | 5 | 5 | 5 |
|   | 10 | 0 | 5 | 5 | 5 |
|   | 5 | 0 | 4 | 5 | 4 |
| 56 | 20 | 0 | 5 | 5 | 5 |

TABLE 1-continued

| Compound No. | Dosage (weight of active ingredient, g/are) | Phytotoxicity Rice plant | Herbicidal activity Barnyard grass | Herbicidal activity Broad-leaved weeds | Nut-sedge |
|---|---|---|---|---|---|
| 57 | 10 | 0 | 5 | 5 | 5 |
|  | 20 | 0 | 5 | 5 | 5 |
| 58 | 10 | 0 | 4 | 5 | 5 |
|  | 20 | 0 | 5 | 5 | 5 |
| 59 | 10 | 0 | 4 | 5 | 5 |
|  | 20 | 0 | 4 | 5 | 5 |
| 60 | 10 | 0 | 4 | 5 | 5 |
|  | 20 | 0 | 5 | 5 | 5 |
| 61 | 10 | 0 | 4 | 5 | 5 |
|  | 20 | 0 | 4 | 5 | 5 |
| 62 | 10 | 0 | 4 | 5 | 5 |
|  | 20 | 0 | 5 | 5 | 5 |
| 63 | 10 | 0 | 4 | 5 | 5 |
|  | 20 | 0 | 5 | 5 | 5 |
| 64 | 10 | 0 | 4 | 5 | 5 |
|  | 20 | 0 | 5 | 5 | 5 |
| 65 | 10 | 0 | 4 | 5 | 5 |
|  | 20 | 0 | 4 | 5 | 5 |
| 66 | 10 | 0 | 4 | 5 | 5 |
|  | 20 | 0 | 5 | 5 | 5 |
| 67 | 10 | 0 | 5 | 5 | 5 |
|  | 20 | 0 | 5 | 5 | 5 |
| 68 | 10 | 0 | 4 | 5 | 5 |
|  | 20 | 0 | 5 | 5 | 5 |
| 69 | 10 | 0 | 5 | 5 | 5 |
|  | 20 | 0 | 5 | 5 | 5 |
| 70 | 10 | 0 | 5 | 5 | 5 |
|  | 20 | 0 | 5 | 5 | 5 |
| 71 | 10 | 0 | 5 | 5 | 5 |
|  | 20 | 1 | 5 | 5 | 5 |
| 72 | 10 | 0 | 5 | 5 | 5 |
|  | 20 | 1 | 5 | 5 | 5 |
| 73 | 10 | 0 | 4 | 5 | 5 |
|  | 20 | 0 | 5 | 5 | 5 |
| 74 | 10 | 0 | 4 | 5 | 5 |
|  | 20 | 0 | 4 | 5 | 5 |
| 75 | 10 | 0 | 4 | 5 | 5 |
|  | 20 | 0 | 5 | 5 | 5 |
| 76 | 10 | 0 | 4 | 5 | 5 |
|  | 20 | 0 | 5 | 5 | 5 |
| 77 | 10 | 0 | 5 | 5 | 5 |
|  | 20 | 0 | 5 | 5 | 5 |
| 78 | 10 | 0 | 4 | 5 | 5 |
|  | 20 | 0 | 5 | 5 | 5 |
| 79 | 10 | 0 | 3 | 5 | 5 |
|  | 20 | 0 | 4 | 5 | 5 |
| 80 | 10 | 0 | 4 | 5 | 5 |
|  | 20 | 0 | 5 | 5 | 5 |
| 81 | 10 | 0 | 4 | 5 | 5 |
|  | 20 | 0 | 5 | 5 | 5 |
| 82 | 10 | 0 | 5 | 5 | 5 |
|  | 20 | 0 | 5 | 5 | 5 |
| 83 | 10 | 0 | 4 | 5 | 5 |
|  | 20 | 0 | 5 | 5 | 5 |
| 84 | 10 | 0 | 5 | 5 | 5 |
|  | 20 | 0 | 5 | 5 | 5 |
| 85 | 10 | 0 | 3 | 5 | 5 |
|  | 20 | 0 | 4 | 5 | 5 |
| 86 | 10 | 0 | 5 | 5 | 5 |
|  | 20 | 1 | 5 | 5 | 5 |
| 87 | 10 | 0 | 3 | 5 | 5 |
|  | 20 | 0 | 4 | 5 | 5 |
| 88 | 10 | 0 | 4 | 5 | 5 |
|  | 20 | 0 | 4 | 5 | 5 |
| 89 | 10 | 0 | 4 | 5 | 5 |
|  | 20 | 0 | 4 | 5 | 5 |
| 93 | 10 | 0 | 5 | 5 | 5 |
|  | 20 | 0 | 5 | 5 | 5 |
| 95 | 10 | 0 | 3 | 5 | 5 |
|  | 20 | 0 | 4 | 5 | 5 |
| 96 | 10 | 0 | 4 | 5 | 5 |
|  | 20 | 0 | 5 | 5 | 5 |
| 99 | 10 | 0 | 4 | 5 | 5 |
|  | 20 | 0 | 4 | 5 | 5 |
| 100 | 20 | 0 | 5 | 5 | 5 |
| 102 | 10 | 0 | 4 | 5 | 5 |
|  | 20 | 0 | 4 | 5 | 5 |
| 103 | 10 | 0 | 4 | 5 | 5 |
|  | 20 | 0 | 3 | 5 | 5 |
| 104 | 10 | 0 | 5 | 5 | 5 |
|  | 20 | 0 | 3 | 5 | 5 |
| 105 | 10 | 0 | 4 | 5 | 5 |
|  | 20 | 0 | 3 | 5 | 5 |
| 106 | 10 | 0 | 5 | 5 | 5 |
|  | 20 | 0 | 4 | 5 | 5 |
| 107 | 10 | 0 | 4 | 5 | 5 |
|  | 20 | 0 | 4 | 5 | 5 |
| 109 | 10 | 0 | 4 | 5 | 5 |
|  | 20 | 0 | 3 | 5 | 5 |
| 111 | 10 | 0 | 4 | 5 | 5 |
|  | 20 | 0 | 4 | 5 | 5 |
| 112 | 10 | 0 | 5 | 5 | 5 |
|  | 20 | 0 | 5 | 5 | 5 |
| 113 | 10 | 0 | 4 | 5 | 5 |
|  | 20 | 0 | 3 | 5 | 5 |
| 117 | 10 | 0 | 5 | 5 | 5 |
|  | 20 | 0 | 4 | 5 | 5 |
| 119 | 10 | 0 | 5 | 5 | 5 |
|  | 20 | 0 | 5 | 5 | 5 |
| 120 | 10 | 0 | 4 | 5 | 5 |
|  | 20 | 0 | 4 | 5 | 5 |
| 124 | 10 | 0 | 4 | 5 | 5 |
|  | 20 | 0 | 4 | 5 | 5 |
| 127 | 10 | 0 | 4 | 5 | 5 |
|  | 20 | 0 | 4 | 5 | 5 |
| 130 | 10 | 0 | 3 | 5 | 5 |
|  | 20 | 0 | 4 | 5 | 5 |
| 132 | 10 | 0 | 4 | 5 | 5 |
|  | 20 | 0 | 4 | 5 | 5 |
| 136 | 10 | 0 | 5 | 5 | 5 |
|  | 20 | 0 | 5 | 5 | 5 |
| 137 | 10 | 0 | 5 | 5 | 5 |
|  | 20 | 0 | 5 | 5 | 5 |
| 139 | 10 | 0 | 4 | 5 | 5 |
|  | 20 | 0 | 4 | 5 | 5 |
| 140 | 10 | 0 | 3 | 5 | 5 |
|  | 20 | 0 | 4 | 5 | 5 |
| 141 | 10 | 0 | 4 | 5 | 5 |
|  | 20 | 0 | 5 | 5 | 5 |
| 142 | 10 | 0 | 5 | 5 | 5 |
|  | 20 | 0 | 5 | 5 | 5 |
| 143 | 10 | 0 | 4 | 5 | 5 |
|  | 20 | 0 | 4 | 5 | 5 |
| Control (a) | 5 | 0 | 2 | 4 | 3 |
|  | 10 | 0 | 2 | 5 | 3 |
|  | 20 | 1 | 3 | 5 | 4 |
| MCP | 5 | 1 | 2 | 5 | 5 |
|  | 10 | 2 | 3 | 5 | 5 |
|  | 20 | 3 | 4 | 5 | 5 |

EXAMPLE II

Herbicidal Activity by Foliar Application

Plastic pots (35×25×10 cm) were filled with upland field soil, and the seeds of cocklebur, radish, redroot pigweed, common lambsquarter, nightshade, sunflower, morning glory, large crabgrass, green foxtail and barnyard grass were sowed in each of the pots and grown for 3 weeks in a greenhouse. The designed amount of the test compound was sprayed to the foliage over the top of the test plants by means of a small hand sprayer. At the time of application, the test plants were at two to four leaf stages and 2 to 10 cm in height with variations depending on the kinds of the test plants.

After the spraying, the test plants were placed in the greenhouse for an additional 3 weeks, and herbicidal activity was evaluated as in Example I. The results are shown in Table 2. In the above foliar application, the designed amount of the test compound was formulated into an emulsifiable concentrate, dispersed in water containing a wetting agent and sprayed at a volume of 5 liters per are.

TABLE 2

| Compound No. | Dosage (weight of active ingredient, g/are) | Herbicidal activity | | | | | | | | |
|---|---|---|---|---|---|---|---|---|---|---|
| | | Cocklebur | Radish | Redroot pigweed | Common lambs-quarter | Night-shade | Sunflower | Morning glory | Large crab grass | Green foxtail | Barnyard grass |
| 1 | 20 | 5 | 5 | 5 | 5 | 5 | 5 | 5 | 5 | 4 | 4 |
| | 10 | 5 | 5 | 5 | 5 | 5 | 5 | 5 | 3 | 3 | 3 |
| 2 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 3 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 4 |
| 4 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 5 |
| 5 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 6 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| 7 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| 8 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 9 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 3 |
| 10 | 20 | 5 | 5 | 5 | 5 | 5 | 5 | 5 | 5 | 4 | 4 |
| | 10 | 5 | 5 | 5 | 5 | 5 | 5 | 5 | 3 | 4 | 3 |
| 11 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| 12 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 3 |
| 13 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 4 |
| 14 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |

| Compound No. | Dosage (weight of active ingredient, g/are) | Herbicidal activity | | | | | | | | |
|---|---|---|---|---|---|---|---|---|---|---|
| | | Cocklebur | Radish | Redroot pigweed | Common lambs-quarter | Night-shade | Sunflower | Annual morning glory | Large crab-grass | Foxtail | Barnyard grass |
| 15 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 4 | 5 | 5 |
| 16 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 5 |
| 17 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 4 |
| 18 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 4 |
| 19 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 5 |
| | 5 | 5 | 5 | 5 | 5 | 5 | 5 | 5 | 3 | 3 | 4 |
| 20 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 4 |
| 21 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 4 | 5 |
| 22 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 5 |
| 23 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 4 | 5 | 5 | 5 | 4 | 5 |
| 24 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| | 5 | 5 | 5 | 5 | 5 | 5 | 5 | 5 | 4 | 5 | 4 |
| 25 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 5 |
| 26 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 5 |
| 27 | 20 | 5 | 5 | 5 | 5 | 5 | 5 | 5 | 4 | 5 | 5 |
| | 10 | 5 | 5 | 5 | 5 | 5 | 5 | 5 | 4 | 5 | 5 |

TABLE 2-continued

| | | | | | | | | | | | |
|---|---|---|---|---|---|---|---|---|---|---|---|
| | 5 | 5 | 5 | 5 | 5 | 5 | 5 | 5 | 3 | 3 | 5 |
| 28 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 5 |
| 29 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| | 5 | 5 | 5 | 5 | 5 | 5 | 5 | 4 | 4 | 4 | 3 |
| 30 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 4 | 5 | 4 | 4 |
| 31 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 4 |
| 32 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| | 5 | 5 | 5 | 5 | 5 | 5 | 5 | 5 | 5 | 5 | 4 |
| 34 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 5 |
| | 5 | 5 | 5 | 5 | 5 | 5 | 5 | 5 | 3 | 3 | 5 |
| 35 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 4 |
| 36 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 4 |
| 37 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 4 |
| 38 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| | 5 | 5 | 5 | 5 | 5 | 5 | 5 | 4 | 5 | 5 | 3 |
| 39 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 4 | 5 |
| 40 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 5 |
| 42 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 5 | 3 |
| 43 | 20 | 5 | 5 | 5 | 5 | 5 | 5 | 5 | 5 | 5 | 5 |
| | 10 | 5 | 5 | 5 | 5 | 5 | 5 | 5 | 5 | 3 | 5 |
| | 5 | 5 | 5 | 5 | 5 | 5 | 5 | 5 | 5 | 3 | 4 |
| 44 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 4 |
| | 5 | 5 | 5 | 5 | 5 | 5 | 5 | 5 | 4 | 4 | 3 |
| 45 | 20 | 5 | 5 | 5 | 5 | 5 | 5 | 5 | 5 | 5 | 5 |
| | 10 | 5 | 5 | 5 | 5 | 5 | 5 | 4 | 5 | 5 | 5 |
| | 5 | 5 | 5 | 5 | 5 | 3 | 5 | 2 | 5 | 4 | 5 |
| 47 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 3 | 5 | 4 | 5 |
| 48 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 4 | 5 | 4 |
| 49 | 20 | 5 | 5 | 5 | 5 | 5 | 5 | 5 | 5 | 5 | 5 |
| | 10 | 5 | 5 | 5 | 5 | 4 | 5 | 5 | 5 | 4 | 4 |
| | 5 | 5 | 5 | 5 | 5 | 3 | 5 | 5 | 5 | 3 | 4 |
| 50 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 5 |
| | 5 | 5 | 5 | 5 | 5 | 5 | 5 | 4 | 4 | 3 | 5 |
| 52 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| | 5 | 5 | 5 | 5 | 5 | 5 | 5 | 4 | 4 | 4 | 4 |
| 53 | 20 | 5 | 5 | 5 | 5 | 5 | 5 | 5 | 5 | 5 | 5 |
| | 10 | 5 | 5 | 5 | 5 | 5 | 5 | 4 | 5 | 5 | 5 |
| | 5 | 5 | 5 | 5 | 5 | 5 | 5 | 4 | 4 | 5 | 3 |
| 54 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 4 | 4 | 5 |
| 55 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 3 | 4 | 4 |
| 56 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 57 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 5 |
| 58 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 59 | 20 | 5 | 5 | 5 | 5 | 5 | 5 | 5 | 5 | 4 | 3 |
| | 10 | 5 | 5 | 5 | 5 | 5 | 5 | 5 | 3 | 4 | 3 |
| 60 | 20 | 5 | 5 | 5 | 5 | 5 | 5 | 5 | 5 | 5 | 5 |

TABLE 2-continued

| | | | | | | | | | | | |
|---|---|---|---|---|---|---|---|---|---|---|---|
| 61 | 10 | 5 | 5 | 5 | 5 | 5 | 5 | 5 | 4 | 5 | 4 |
| | 20 | 5 | 5 | 5 | 5 | 5 | 5 | 5 | 5 | 4 | 4 |
| 62 | 10 | 5 | 5 | 5 | 5 | 5 | 5 | 5 | 3 | 4 | 5 |
| | 20 | 5 | 5 | 5 | 5 | 5 | 5 | 5 | 4 | 5 | 4 |
| 63 | 10 | 5 | 5 | 5 | 5 | 5 | 5 | 5 | 5 | 5 | 5 |
| | 20 | 5 | 5 | 5 | 5 | 5 | 5 | 5 | 5 | 5 | 5 |
| 64 | 10 | 5 | 5 | 5 | 5 | 5 | 5 | 5 | 5 | 4 | 4 |
| | 20 | 5 | 5 | 5 | 5 | 5 | 5 | 5 | 5 | 5 | 5 |
| 65 | 10 | 5 | 5 | 5 | 5 | 5 | 5 | 5 | 5 | 5 | 5 |
| | 20 | 5 | 5 | 5 | 5 | 5 | 5 | 5 | 5 | 4 | 4 |
| 68 | 10 | 5 | 5 | 5 | 5 | 5 | 5 | 5 | 5 | 5 | 5 |
| | 20 | 5 | 5 | 5 | 5 | 5 | 5 | 5 | 5 | 4 | 5 |
| 69 | 10 | 5 | 5 | 5 | 5 | 5 | 5 | 5 | 5 | 5 | 5 |
| | 20 | 5 | 5 | 5 | 5 | 5 | 5 | 5 | 5 | 5 | 5 |
| 70 | 10 | 5 | 5 | 5 | 5 | 5 | 5 | 5 | 5 | 5 | 5 |
| | 20 | 5 | 5 | 5 | 5 | 5 | 5 | 5 | 5 | 5 | 5 |
| 71 | 10 | 5 | 5 | 5 | 5 | 5 | 5 | 5 | 5 | 5 | 5 |
| | 20 | 5 | 5 | 5 | 5 | 5 | 5 | 5 | 5 | 5 | 5 |
| 72 | 10 | 5 | 5 | 5 | 5 | 5 | 5 | 5 | 5 | 5 | 5 |
| | 20 | 5 | 5 | 5 | 5 | 5 | 5 | 5 | 5 | 5 | 5 |
| 73 | 10 | 5 | 5 | 5 | 5 | 5 | 5 | 5 | 5 | 5 | 5 |
| | 20 | 5 | 5 | 5 | 5 | 5 | 5 | 5 | 5 | 5 | 4 |
| 74 | 10 | 5 | 5 | 5 | 5 | 5 | 5 | 5 | 5 | 5 | 5 |
| | 20 | 5 | 5 | 5 | 5 | 5 | 5 | 5 | 5 | 4 | 4 |
| 75 | 10 | 5 | 5 | 5 | 5 | 5 | 5 | 5 | 5 | 5 | 5 |
| | 20 | 5 | 5 | 5 | 5 | 5 | 5 | 5 | 4 | 5 | 5 |
| 76 | 10 | 5 | 5 | 5 | 5 | 5 | 5 | 5 | 5 | 5 | 5 |
| | 20 | 5 | 5 | 5 | 5 | 5 | 5 | 5 | 4 | 4 | 5 |
| 77 | 10 | 5 | 5 | 5 | 5 | 5 | 5 | 5 | 5 | 5 | 5 |
| | 20 | 5 | 5 | 5 | 5 | 5 | 5 | 5 | 5 | 5 | 5 |
| 78 | 10 | 5 | 5 | 5 | 5 | 5 | 5 | 5 | 5 | 5 | 4 |
| | 20 | 5 | 5 | 5 | 5 | 5 | 5 | 5 | 5 | 4 | 4 |
| 79 | 10 | 5 | 5 | 5 | 5 | 5 | 5 | 5 | 3 | 4 | 3 |
| | 20 | 5 | 5 | 5 | 5 | 5 | 5 | 5 | 5 | 5 | 5 |
| 80 | 10 | 5 | 5 | 5 | 5 | 5 | 5 | 5 | 5 | 5 | 5 |
| | 20 | 5 | 5 | 5 | 5 | 5 | 5 | 5 | 5 | 5 | 5 |
| 81 | 10 | 5 | 5 | 5 | 5 | 5 | 5 | 5 | 5 | 5 | 5 |
| | 20 | 5 | 5 | 5 | 5 | 5 | 5 | 5 | 5 | 5 | 5 |
| 83 | 10 | 5 | 5 | 5 | 5 | 5 | 5 | 5 | 5 | 4 | 5 |
| | 20 | 5 | 5 | 5 | 5 | 5 | 5 | 5 | 5 | 5 | 5 |
| 84 | 10 | 5 | 5 | 5 | 5 | 5 | 5 | 5 | 4 | 5 | 5 |
| | 20 | 5 | 5 | 5 | 5 | 5 | 5 | 5 | 5 | 5 | 5 |
| 85 | 10 | 5 | 5 | 5 | 5 | 5 | 5 | 5 | 4 | 5 | 4 |
| | 20 | 5 | 5 | 5 | 5 | 5 | 5 | 5 | 5 | 5 | 5 |
| 86 | 10 | 5 | 5 | 5 | 5 | 5 | 5 | 5 | 5 | 5 | 5 |
| | 20 | 5 | 5 | 5 | 5 | 5 | 5 | 5 | 5 | 5 | 5 |
| 87 | 10 | 5 | 5 | 5 | 5 | 5 | 5 | 5 | 5 | 5 | 4 |
| | 20 | 5 | 5 | 5 | 5 | 5 | 5 | 5 | 5 | 5 | 5 |
| 88 | 10 | 5 | 5 | 5 | 5 | 5 | 5 | 5 | 4 | 5 | 4 |
| | 20 | 5 | 5 | 5 | 5 | 5 | 5 | 5 | 4 | 5 | 5 |
| 91 | 10 | 5 | 5 | 5 | 5 | 5 | 5 | 5 | 4 | 4 | 3 |
| | 20 | 5 | 5 | 5 | 5 | 5 | 5 | 5 | 5 | 5 | 5 |
| 93 | 10 | 5 | 5 | 5 | 5 | 5 | 5 | 5 | 5 | 5 | 4 |
| | 20 | 5 | 5 | 5 | 5 | 5 | 5 | 5 | 5 | 5 | 5 |
| 94 | 10 | 5 | 5 | 5 | 5 | 5 | 5 | 5 | 5 | 4 | 5 |
| | 20 | 5 | 5 | 5 | 5 | 5 | 5 | 5 | 5 | 5 | 5 |
| 95 | 10 | 5 | 5 | 5 | 5 | 5 | 5 | 5 | 4 | 4 | 3 |
| | 20 | 5 | 5 | 5 | 5 | 5 | 5 | 5 | 5 | 5 | 5 |
| 96 | 10 | 5 | 5 | 5 | 5 | 5 | 5 | 5 | 5 | 4 | 5 |
| | 20 | 5 | 5 | 5 | 5 | 5 | 5 | 5 | 5 | 5 | 5 |
| 99 | 10 | 5 | 5 | 5 | 5 | 5 | 5 | 5 | 4 | 4 | 5 |
| | 20 | 5 | 5 | 5 | 5 | 5 | 5 | 5 | 4 | 5 | 4 |
| 101 | 10 | 5 | 5 | 5 | 5 | 5 | 5 | 5 | 4 | 4 | 4 |
| | 20 | 5 | 5 | 5 | 5 | 5 | 5 | 5 | 5 | 4 | 5 |
| 103 | 10 | 5 | 5 | 5 | 5 | 5 | 5 | 5 | 4 | 4 | 3 |
| | 20 | 5 | 5 | 5 | 5 | 5 | 5 | 5 | 5 | 5 | 5 |
| 104 | 10 | 5 | 5 | 5 | 5 | 5 | 5 | 5 | 4 | 4 | 5 |
| | 20 | 5 | 5 | 5 | 5 | 5 | 5 | 5 | 5 | 4 | 4 |
| 105 | 10 | 5 | 5 | 5 | 5 | 5 | 5 | 5 | 4 | 4 | 3 |
| | 20 | 5 | 5 | 5 | 5 | 5 | 5 | 5 | 5 | 5 | 5 |
| 106 | 10 | 5 | 5 | 5 | 5 | 5 | 5 | 5 | 5 | 5 | 4 |
| | 20 | 5 | 5 | 5 | 5 | 5 | 5 | 5 | 4 | 5 | 4 |
| 109 | 10 | 5 | 5 | 5 | 5 | 5 | 5 | 5 | 4 | 3 | 5 |
| | 20 | 5 | 5 | 5 | 5 | 5 | 5 | 5 | 5 | 4 | 5 |
| 110 | 10 | 5 | 5 | 5 | 5 | 5 | 5 | 5 | 4 | 4 | 3 |
| | 20 | 5 | 5 | 5 | 5 | 5 | 5 | 5 | 5 | 5 | 5 |
| 112 | 10 | 5 | 5 | 5 | 5 | 5 | 5 | 5 | 5 | 4 | 5 |
| | 20 | 5 | 5 | 5 | 5 | 5 | 5 | 5 | 4 | 4 | 5 |
| 113 | 10 | 5 | 5 | 5 | 5 | 5 | 5 | 5 | 4 | 4 | 3 |
| | 20 | 5 | 5 | 5 | 5 | 5 | 5 | 5 | 5 | 5 | 5 |
| 116 | | | | | | | | | | | |

TABLE 2-continued

| | | | | | | | | | | | |
|---|---|---|---|---|---|---|---|---|---|---|---|
| | 10 | 5 | 5 | 5 | 5 | 5 | 5 | 5 | 4 | 5 | 5 |
| 118 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 4 |
| 121 | 20 | 5 | 5 | 5 | 5 | 5 | 5 | 5 | 5 | 4 | 4 |
| | 10 | 5 | 5 | 5 | 5 | 5 | 5 | 5 | 4 | 4 | 4 |
| 123 | 20 | 5 | 5 | 5 | 5 | 5 | 5 | 5 | 5 | 4 | 4 |
| | 10 | 5 | 5 | 5 | 5 | 5 | 5 | 5 | 3 | 4 | 3 |
| 127 | 20 | 5 | 5 | 5 | 5 | 5 | 5 | 5 | 5 | 5 | 4 |
| | 10 | 5 | 5 | 5 | 5 | 5 | 5 | 5 | 4 | 3 | 4 |
| 130 | 20 | 5 | 5 | 5 | 5 | 5 | 5 | 5 | 5 | 4 | 4 |
| | 10 | 5 | 5 | 5 | 5 | 5 | 5 | 5 | 3 | 4 | 3 |
| 136 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| 137 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| 138 | 20 | 5 | 5 | 5 | 5 | 5 | 5 | 5 | 5 | 4 | 4 |
| | 10 | 5 | 5 | 5 | 5 | 5 | 5 | 5 | 4 | 4 | 4 |
| 141 | 20 | 5 | 5 | 5 | 5 | 5 | 5 | 5 | 4 | 4 | 4 |
| | 10 | 5 | 5 | 5 | 5 | 5 | 5 | 5 | 3 | 4 | 3 |
| 142 | 20 | 5 | 5 | 5 | 5 | 5 | 5 | 5 | 5 | 5 | 4 |
| | 10 | 5 | 5 | 5 | 5 | 5 | 5 | 5 | 4 | 4 | 4 |
| 143 | 20 | 5 | 5 | 5 | 5 | 5 | 5 | 5 | 4 | 5 | 4 |
| | 10 | 5 | 5 | 5 | 5 | 5 | 5 | 5 | 3 | 3 | 3 |
| Control (a) | 20 | 5 | 5 | 5 | 5 | 5 | 5 | 5 | 4 | 4 | 4 |
| | 10 | 5 | 5 | 5 | 5 | 5 | 5 | 5 | 3 | 2 | 3 |
| | 5 | 4 | 5 | 5 | 5 | 4 | 5 | 5 | 1 | 2 | 2 |
| Control (c) | 20 | 5 | 5 | 5 | 5 | 5 | 5 | 4 | 4 | 4 | 4 |
| | 10 | 4 | 5 | 5 | 5 | 5 | 4 | 4 | 3 | 2 | 3 |
| Chloro- | 20 | 5 | 5 | 5 | 5 | 5 | 5 | 5 | 4 | 4 | 4 |
| xuron | 10 | 5 | 5 | 5 | 5 | 5 | 5 | 5 | 3 | 4 | 3 |
| | 5 | 5 | 5 | 5 | 5 | 5 | 5 | 5 | 3 | 2 | 2 |
| Bentazon | 20 | 5 | 5 | 4 | 5 | 5 | 5 | 4 | 1 | 0 | 3 |
| | 10 | 5 | 5 | 3 | 5 | 5 | 5 | 2 | 0 | 0 | 1 |
| | 5 | 5 | 5 | 1 | 4 | 5 | 5 | 1 | 0 | 0 | 0 |

EXAMPLE III

Phytotoxicity on Crop Plants by Foliar Applications

Wagner's pots (1/5000 are) were filled with upland field soil, and the seeds of corn, wheat, cotton or soybean were sowed in separate pots. After being cultivated in a greenhouse for 2 to 3 weeks, the designed amount of the test compound was sprayed to the foliage over the top of the test plants by means of a small hand sprayer. After the spraying, the test plants were grown for an additional 3 weeks, and damage to crop plants was evaluated according to the standard given in Example I. The results are shown in Table 3. In the above foliar application, the designed amount of the test compound was formulated into an emulsifiable concentrate, dispersed in water containing a wetting agent and sprayed at a volume of 5 liters per are. The growth stage of each test plant at the time of application was as follows: corn, 2 leaf stage; wheat, 2 leaf stage; cotton, 1 leaf stage; soybean, 2 leaf stage; sugar beet, 2 leaf stage.

TABLE 3

| Compound No. | Dosage (weight of active ingredient g/are) | Phytotoxicity | | | | | |
|---|---|---|---|---|---|---|---|
| | | Corn | Wheat | Rice plant | Cotton | Soybean | Sugar beet |
| 2 | 20 | 1 | 0 | — | — | — | — |
| | 10 | 1 | 1 | — | — | — | — |
| | 5 | 0 | 0 | — | — | — | — |
| 3 | 20 | — | 1 | — | — | — | — |
| | 10 | — | 0 | — | — | — | — |
| | 5 | — | 0 | — | — | — | — |
| 4 | 20 | — | 1 | — | — | — | — |
| | 10 | — | 1 | — | — | — | — |
| | 5 | — | 0 | — | — | — | — |
| 5 | 20 | 0 | — | — | — | — | — |
| | 10 | 0 | — | — | — | — | — |
| | 5 | 0 | — | — | — | — | — |
| 6 | 20 | — | 1 | — | — | 1 | — |
| | 10 | — | 1 | — | — | 1 | — |
| | 5 | — | 0 | — | — | 0 | — |
| 7 | 20 | 1 | — | — | 1 | 1 | — |
| | 10 | 0 | — | — | 1 | 1 | — |
| | 5 | 0 | — | — | 0 | 0 | — |
| 8 | 20 | 1 | — | — | — | — | — |
| | 10 | 0 | — | — | — | — | — |
| | 5 | 0 | — | — | — | — | — |
| 10 | 20 | 1 | 0 | — | — | 0 | — |
| | 10 | 1 | 0 | — | — | 0 | — |
| | 5 | 0 | 0 | — | — | 0 | — |
| 12 | 20 | — | — | — | — | 1 | — |
| | 10 | — | — | — | — | 0 | — |
| | 5 | — | — | — | — | 0 | — |
| 13 | 20 | — | — | — | — | 1 | — |
| | 10 | — | — | — | — | 1 | — |
| | 5 | — | — | — | — | 0 | — |
| 19 | 20 | — | 1 | — | — | 1 | — |
| | 10 | — | 0 | — | — | 0 | — |
| | 5 | — | 0 | — | — | 0 | — |
| 20 | 20 | 1 | — | — | — | — | — |
| | 10 | 0 | — | — | — | — | — |
| | 5 | 0 | — | — | — | — | — |
| 23 | 20 | — | 1 | — | — | — | — |
| | 10 | — | 1 | — | — | — | — |
| | 5 | — | 0 | — | — | — | — |
| 30 | 20 | — | 0 | — | — | 0 | 1 |
| | 10 | — | 0 | — | — | 0 | 0 |
| | 5 | — | 0 | — | — | 0 | 0 |
| 31 | 20 | 1 | 0 | — | — | — | — |
| | 10 | 1 | 0 | — | — | — | — |
| | 5 | 0 | 0 | — | — | — | — |
| 36 | 20 | 0 | — | — | — | 1 | 1 |
| | 10 | 0 | — | — | — | 0 | 1 |
| | 5 | 0 | — | — | — | 0 | 0 |
| 37 | 20 | 1 | — | — | — | — | — |
| | 10 | 0 | — | — | — | — | — |

TABLE 3-continued

| Compound No. | Dosage (weight of active ingredient g/are) | Corn | Wheat | Rice plant | Cotton | Soybean | Sugar beet |
|---|---|---|---|---|---|---|---|
| 39 | 5 | 0 | — | — | — | — | — |
|  | 20 | 1 | — | — | — | — | — |
|  | 10 | 0 | — | — | — | — | — |
| 40 | 5 | 0 | — | — | — | — | — |
|  | 20 | 1 | — | — | — | — | — |
|  | 10 | 1 | — | — | — | — | — |
| 41 | 5 | 0 | — | — | — | — | — |
|  | 20 | 0 | 0 | — | — | — | — |
|  | 10 | 0 | 0 | — | — | — | — |
|  | 5 | 0 | 0 | — | — | — | — |
| 42 | 20 | — | — | — | — | 0 | — |
|  | 10 | — | — | — | — | 0 | — |
|  | 5 | — | — | — | — | 0 | — |
| 44 | 20 | — | — | — | — | 1 | 1 |
|  | 10 | — | — | — | — | 1 | 0 |
|  | 5 | — | — | — | — | 0 | 0 |
| 45 | 20 | — | — | — | 1 | 1 | — |
|  | 10 | — | — | — | 1 | 0 | — |
|  | 5 | — | — | — | 0 | 0 | — |
| 47 | 20 | — | — | — | — | 1 | — |
|  | 10 | — | — | — | — | 1 | — |
|  | 5 | — | — | — | — | 0 | — |
| 48 | 20 | — | — | — | 1 | — | — |
|  | 10 | — | — | — | 1 | — | — |
|  | 5 | — | — | — | 0 | — | — |
| 49 | 20 | — | 0 | — | — | — | — |
|  | 10 | — | 0 | — | — | — | — |
|  | 5 | — | 0 | — | — | — | — |
| 50 | 20 | — | 1 | — | — | 1 | — |
|  | 10 | — | 0 | — | — | 0 | — |
|  | 5 | — | 0 | — | — | 0 | — |
| 56 | 20 | — | — | — | — | 1 | — |
|  | 10 | — | — | — | — | 1 | — |
| 57 | 20 | — | 0 | 0 | — | 1 | — |
|  | 10 | — | 0 | 0 | — | 0 | — |
| 58 | 20 | 1 | — | 0 | — | — | — |
|  | 10 | 0 | — | 0 | — | — | — |
| 59 | 20 | 0 | 0 | 0 | 1 | 1 | — |
|  | 10 | 0 | 0 | 0 | 0 | 0 | — |
| 61 | 20 | 0 | 0 | — | — | 1 | — |
|  | 10 | 0 | 0 | — | — | 0 | — |
| 62 | 20 | 1 | 0 | — | — | — | 1 |
|  | 10 | 0 | 0 | — | — | — | 0 |
| 64 | 20 | 1 | 0 | — | — | — | — |
|  | 10 | 0 | 0 | — | — | — | — |
| 68 | 20 | — | 0 | — | — | — | — |
|  | 10 | — | 0 | — | — | — | — |
| 69 | 20 | — | 1 | — | — | — | — |
|  | 10 | — | 0 | — | — | — | — |
| 70 | 20 | — | 0 | 1 | — | — | — |
|  | 10 | — | 0 | 0 | — | — | — |
| 74 | 20 | — | 0 | — | — | — | — |
|  | 10 | — | 0 | — | — | — | — |
| 75 | 20 | — | 0 | — | — | — | — |
|  | 10 | — | 0 | — | — | — | — |
| 76 | 20 | — | 1 | 0 | — | — | — |
|  | 10 | — | 0 | 0 | — | — | — |
| 77 | 20 | — | 1 | 0 | — | 1 | — |
|  | 10 | — | 0 | 0 | — | 0 | — |
| 78 | 20 | — | 0 | 0 | — | 0 | — |
|  | 10 | — | 0 | 0 | — | 0 | — |
| 79 | 20 | 1 | — | — | 0 | 0 | — |
|  | 10 | 0 | — | — | 0 | 0 | — |
| 80 | 20 | — | — | 1 | 0 | 0 | — |
|  | 10 | — | — | 0 | 0 | 0 | — |
| 82 | 20 | — | — | — | 0 | 0 | — |
|  | 10 | — | — | — | 0 | 0 | — |
| 85 | 20 | — | — | — | 0 | 0 | — |
|  | 10 | — | — | — | 0 | 0 | — |
| 86 | 20 | — | — | 1 | — | — | — |
|  | 10 | — | — | 0 | — | — | — |
| 87 | 20 | — | 0 | — | 0 | 0 | — |
|  | 10 | — | 0 | — | 0 | 0 | — |
| 88 | 20 | — | 0 | 0 | — | — | — |
|  | 10 | — | 0 | 0 | — | — | — |
| 95 | 20 | 0 | 0 | — | — | 0 | — |
|  | 10 | 0 | 0 | — | — | 0 | — |
| 96 | 20 | — | 0 | 0 | — | 0 | — |
|  | 10 | — | 0 | 0 | — | 0 | — |
| 103 | 20 | — | — | — | — | — | 1 |
|  | 10 | — | — | — | — | — | 1 |
| 104 | 20 | — | 0 | — | — | — | 1 |
|  | 10 | — | 0 | — | — | — | 0 |
| 105 | 20 | — | — | — | — | — | 0 |
|  | 10 | — | — | — | — | — | 0 |
| 106 | 20 | 1 | 0 | — | — | 0 | 0 |
|  | 10 | 0 | 0 | — | — | 0 | 0 |
| 109 | 20 | — | 0 | — | 0 | 1 | — |
|  | 10 | — | 0 | — | 0 | 0 | — |
| 141 | 20 | — | 0 | — | 0 | 1 | — |
|  | 10 | — | 0 | — | 0 | 0 | — |
| 142 | 20 | — | 0 | — | — | 1 | — |
|  | 10 | — | 0 | — | — | 0 | — |
| Control (a) | 20 | — | — | — | 5 | 5 | — |
|  | 10 | — | — | — | 5 | 5 | — |
|  | 5 | — | — | — | 4 | 5 | — |
| Control (b) | 20 | — | — | — | 5 | 5 | — |
|  | 10 | — | — | — | 5 | 5 | — |
| Control (c) | 20 | — | — | — | 5 | 3 | — |
|  | 10 | — | — | — | 5 | 3 | — |
| Atrazine | 20 | 1 | — | — | — | — | — |
|  | 10 | 1 | — | — | — | — | — |
|  | 5 | 0 | — | — | — | — | — |
| Diuron | 20 | 5 | 5 | — | — | — | 5 |
|  | 10 | 5 | 5 | — | — | — | 5 |
|  | 5 | 3 | 4 | — | — | — | 5 |
| Chloroxuron | 20 | — | — | — | — | 3 | — |
|  | 10 | — | — | — | — | 2 | — |
|  | 5 | — | — | — | — | 2 | — |
| Fluometuron | 20 | — | — | — | 3 | — | — |
|  | 10 | — | — | — | 2 | — | — |
|  | 5 | — | — | — | 0 | — | — |
| 2,4-D | 20 | — | 1 | — | — | — | — |
|  | 10 | — | 1 | — | — | — | — |
|  | 5 | — | 0 | — | — | — | — |
| Barban | 20 | — | 3 | — | — | — | — |
|  | 10 | — | 2 | — | — | — | — |
|  | 5 | — | 1 | — | — | — | — |
| Phenmedipham | 20 | — | — | — | — | — | 1 |
|  | 10 | — | — | — | — | — | 1 |
|  | 5 | — | — | — | — | — | 0 |
| Bentazon | 20 | — | — | 0 | — | 1 | 5 |
|  | 10 | — | — | 0 | — | 0 | 5 |
|  | 5 | — | — | 0 | — | 0 | — |

EXAMPLE IV

Herbicidal Activity and Crop Selectivity of the Invention Compounds [I] by Soil Application Wagner's pots (1/5000 are) were filled with upland field soil, and the seeds of soybean, cotton, corn, wheat, sugar beet, rice, redroot pigweed, common lambsquarter, radish, purslane and large crabgrass were sowed in separate pots. The designed amount of the test compound formulated into a wettable powder was dispersed in water, and sprayed to the soil surface by means of a small hand sprayer at a volume of 10 liters per are. After the spraying, the test plants were placed in a greenhouse for 20 days, and crop damage and herbicidal activity were evaluated. The evaluation was carried out according to the standard given in Example I. The results are shown in Table 4.

TABLE 4

| Compound No. | Dosage (weight of active ingredient, g/are) | Phytotoxicity | | | | | | Herbicidal activity | | | | |
|---|---|---|---|---|---|---|---|---|---|---|---|---|
| | | Soybean | Cotton | Sugar beet | Corn | Wheat | Rice plant | Redroot pigweed | Common lambs-quarter | Radish | Purslane | Large crabgrass |
| 4 | 30 | 0 | 0 | — | 0 | 0 | — | 5 | 5 | 5 | 5 | 5 |
| | 20 | 0 | 0 | — | 0 | 0 | — | 5 | 5 | 5 | 4 | 5 |
| 8 | 30 | 0 | 0 | — | 1 | 0 | — | 5 | 5 | 5 | 5 | 5 |
| | 20 | 0 | 0 | — | 0 | 0 | — | 5 | 5 | 5 | 5 | 5 |
| 9 | 30 | 0 | 0 | — | 0 | 0 | — | 5 | 5 | 5 | 5 | 5 |
| | 20 | 0 | 0 | — | 0 | 0 | — | 5 | 5 | 5 | 5 | 5 |
| 12 | 30 | 0 | 0 | — | 0 | 0 | — | 5 | 5 | 5 | 5 | 5 |
| | 20 | 0 | 0 | — | 0 | 0 | — | 5 | 5 | 5 | 5 | 4 |
| 18 | 30 | 0 | 0 | — | 0 | 0 | — | 5 | 5 | 5 | 5 | 5 |
| | 20 | 0 | 0 | — | 0 | 0 | — | 5 | 5 | 5 | 5 | 5 |
| 21 | 30 | 0 | 0 | — | 0 | 0 | — | 5 | 5 | 5 | 5 | 5 |
| | 20 | 0 | 0 | — | 0 | 0 | — | 5 | 5 | 5 | 5 | 5 |
| 23 | 30 | 0 | 0 | — | 0 | 0 | — | 5 | 5 | 5 | 5 | 5 |
| | 20 | 0 | 0 | — | 0 | 0 | — | 5 | 5 | 5 | 5 | 4 |
| 26 | 30 | 0 | 0 | — | 0 | 0 | — | 5 | 5 | 5 | 5 | 5 |
| | 20 | 0 | 0 | — | 0 | 0 | — | 5 | 5 | 5 | 5 | 4 |
| 32 | 30 | 0 | 0 | — | 0 | 0 | — | 5 | 5 | 5 | 5 | 5 |
| | 20 | 0 | 0 | — | 0 | 0 | — | 5 | 5 | 5 | 5 | 3 |
| 36 | 30 | 0 | 0 | — | 0 | 0 | — | 5 | 5 | 5 | 5 | 5 |
| | 20 | 0 | 0 | — | 0 | 0 | — | 5 | 5 | 5 | 5 | 3 |
| 48 | 30 | 0 | 0 | — | 0 | 0 | — | 5 | 5 | 5 | 5 | 5 |
| | 20 | 0 | 0 | — | 0 | 0 | — | 5 | 5 | 5 | 5 | 4 |
| 50 | 30 | 0 | 0 | — | 0 | 0 | — | 5 | 5 | 5 | 5 | 4 |
| | 20 | 0 | 0 | — | 0 | 0 | — | 5 | 5 | 5 | 5 | 4 |
| 56 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 57 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 4 |
| 58 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 62 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 4 |
| 63 | 40 | 0 | 0 | 0 | 0 | 0 | 0 | 5 | 5 | 5 | 5 | 4 |
| | 20 | 0 | 0 | 0 | 0 | 0 | 0 | 5 | 5 | 5 | 5 | 4 |
| 64 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 69 | 40 | 0 | 0 | 1 | 0 | 0 | 0 | 5 | 5 | 5 | 5 | 5 |
| | 20 | 0 | 0 | 0 | 0 | 0 | 0 | 5 | 5 | 5 | 5 | 5 |
| 70 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 72 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 77 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 4 |
| 80 | 40 | 0 | 0 | 0 | 0 | 0 | 0 | 5 | 5 | 5 | 5 | 4 |
| | 20 | 0 | 0 | 0 | 0 | 0 | 0 | 5 | 5 | 5 | 5 | 4 |
| 86 | 40 | 0 | 0 | 0 | 0 | 0 | 0 | 5 | 5 | 5 | 5 | 4 |
| | 20 | 0 | 0 | 0 | 0 | 0 | 0 | 5 | 5 | 5 | 5 | 4 |
| 96 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 4 |
| 99 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 106 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 136 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 142 | 40 | 0 | 0 | 0 | 0 | 0 | 0 | 5 | 5 | 5 | 5 | 4 |
| | 20 | 0 | 0 | 0 | 0 | 0 | 0 | 5 | 5 | 5 | 5 | 4 |
| Chloramben | 20 | 0 | 4 | — | 3 | 1 | — | 2 | 2 | 0 | 5 | 3 |
| | 10 | 0 | 4 | — | 2 | 0 | — | 2 | 1 | 0 | 5 | 2 |
| Diuron | 20 | 5 | 3 | — | 5 | 5 | — | 5 | 5 | 5 | 5 | 5 |
| | 10 | 4 | 1 | — | 3 | 4 | — | 5 | 5 | 5 | 5 | 5 |

EXAMPLE V

Residual Phytotoxicity

Plastic pots (35×25×10 cm) were filled with upland field soil, and a designed amount of the test compound in a wettable powder preparation was dispersed in water to make a volume of 5 liters per are and the dispersion was sprayed over the soil by the aid of a small hand sprayer. The pots were allowed to stand outdoors, and one month or three months thereafter the seeds of wheat and soybean were sowed therein. Then, the test plants were grown outdoors, and the aerial parts of the test plants were cut off. The dry weight of the cut parts was measured and compared with that of the plants in the untreated plots grown under the same conditions as above. The phytotoxicity was evaluated by the same standard as in Example I. The results are shown in Table 5.

TABLE 5

| Compound No. | Dosage (weight of active ingredient, g/are) | Phytotoxicity in case of sowing 1 month after application | | Phytotoxicity in case of sowing 3 months after application | |
| --- | --- | --- | --- | --- | --- |
| | | Wheat | Soybean | Wheat | Soybean |
| 96 | 40 | 0 | 0 | 0 | 0 |
| | 20 | 0 | 0 | 0 | 0 |
| 104 | 40 | 0 | 0 | 0 | 0 |
| | 20 | 0 | 0 | 0 | 0 |
| 106 | 40 | 0 | 0 | 0 | 0 |
| | 20 | 0 | 0 | 0 | 0 |
| Atrazine | 20 | 5 | 5 | 5 | 5 |
| | 10 | 5 | 5 | 5 | 5 |

What is claimed is:

1. A compound of the formula:

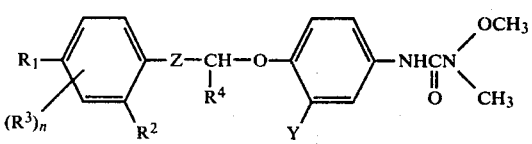

wherein $R^1$, $R^2$ and $R^3$ are each hydrogen, lower alkyl, lower alkoxy, lower alkylthio, halogen or trifluoromethyl, $R^4$ is hydrogen or lower alkyl, Y is hydrogen or halogen, Z is a straight or branched alkylene chain of not more than 8 carbon atoms or an alkylene chain of not more than 8 carbon atoms having one or two atoms of oxygen and/or sulfur inside and/or at the end thereof, and n is an integer of 1 to 3, with the following provisos:
   (a) when $R^1$ is lower alkyl or lower alkoxy, $R^2$ is hydrogen or methyl, $R^4$ is hydrogen, Y is hydrogen and Z is methylene, $R^3$ is lower alkyl, lower alkoxy, halogen or trifluoromethyl;
   (b) when $R^1$ is hydrogen, halogen or trifluoromethyl, $R^4$ is hydrogen, Y is hydrogen and Z is methylene, $R^2$ and $R^3$ are each hydrogen, lower alkyl, lower alkoxy, halogen or trifluoromethyl;
   (c) when $R^4$ is hydrogen, Y is halogen and Z is methylene, $R^1$, $R^2$ and $R^3$ are each hydrogen, lower alkyl, lower alkoxy, halogen or trifluoromethyl;
   (d) when $R^4$ is hydrogen, Z is a straight or branched alkylene chain of 2 to 8 carbon atoms or a straight or branched alkylene chain of 1 to 7 carbon atoms having one or two atoms of oxygen and/or sulfur inside and/or at the end thereof; and
   (e) when $R^4$ is lower alkyl, Z is a straight or branched alkylene chain of 1 to 8 carbon atoms or a straight or branched chain of 1 to 7 carbon atoms having one or two atoms of oxygen and/or sulfur inside and/or at the end thereof.

2. The compound according to claim 1, wherein $R^1$, $R^2$ and $R^3$ are each hydrogen, lower alkyl, lower alkoxy, halogen or trifluoromethyl, $R^4$ is hydrogen, Y is hydrogen and Z is methylene, provided that when $R^1$ is lower alkyl or lower alkoxy and $R^2$ is hydrogen or methyl, $R^3$ is lower alkyl, lower alkoxy, halogen or trifluoromethyl.

3. The compound according to claim 2, wherein no less than one of $R^1$, $R^2$ and $R^3$ is halogen.

4. The compound according to claim 2, wherein $R^1$ is hydrogen, $R^2$ is hydrogen and $R^3$ is lower alkyl or lower alkoxy.

5. The compound according to claim 2, which is N'-4-[2-(2-methylphenyl)ethoxy]phenyl-N-methoxy-N-methylurea.

6. The compound according to claim 1, wherein $R^1$, $R^2$ and $R^3$ are each hydrogen, lower alkyl, lower alkoxy, halogen or trifluoromethyl, $R^4$ is hydrogen, Y is halogen and Z is methylene.

7. The compound according to claim 6, which is N'-3-chloro-4-[2-(4-methylphenyl)ethoxy]phenyl-N-methoxy-N-methylurea.

8. The compound according to claim 6, which is N'-3-chloro-4-[2-(4-isopropylphenyl)ethoxy]phenyl-N-methoxy-N-methylurea.

9. The compound according to claim 1, wherein Z is a straight or branched alkylene chain of not more than 8 carbon atoms and Y is halogen.

10. The compound according to claim 1, which is N'-4-(3-phenylpropoxy)phenyl-N-methoxy-N-methylurea.

11. A herbicidal composition comprising as an active ingredient a herbicidally effective amount of at least one of the compounds according to claim 1, and an inert carrier.

12. The composition according to claim 11, wherein the concentration of the active ingredient is from about 1 to 80% by weight.

13. A method for controlling weeds which comprises applying a herbicidally effective amount of the compound according to claim 1 to the area where the weeds grow.

14. A method of selectively combating weeds in the cultivation of soybeans, cotton, corn, wheat or rice, which comprises applying a herbicidally effective amount of the compound according to claim 1 to the area where the soybean, corn, cotton, wheat or rice crop is cultivated.

* * * * *